(12) United States Patent
Watanabe

(10) Patent No.: US 12,051,201 B2
(45) Date of Patent: Jul. 30, 2024

(54) IMAGE PROCESSING DEVICE CAPABLE OF ACCURATELY DETERMINING ULCERATIVE COLITIS BY USING A MEDICAL IMAGE AND METHOD OF OPERATING THE SAME

(71) Applicant: FUJIFILM Corporation, Tokyo (JP)

(72) Inventor: Hiroki Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 360 days.

(21) Appl. No.: 17/723,525

(22) Filed: Apr. 19, 2022

(65) Prior Publication Data

US 2022/0237795 A1 Jul. 28, 2022

Related U.S. Application Data

(63) Continuation of application No. PCT/JP2020/036674, filed on Sep. 28, 2020.

(30) Foreign Application Priority Data

Oct. 23, 2019 (JP) .................. 2019-193042

(51) Int. Cl.
*G06T 7/00* (2017.01)
*A61B 5/00* (2006.01)

(52) U.S. Cl.
CPC ............ *G06T 7/0012* (2013.01); *A61B 5/004* (2013.01); *A61B 5/0059* (2013.01); *A61B 5/4216* (2013.01); *G06T 2207/30092* (2013.01)

(58) Field of Classification Search
USPC ................................. 382/128, 131
See application file for complete search history.

(56) References Cited

U.S. PATENT DOCUMENTS 8,994,801 B2 3/2015 Tanaka et al.
11,957,483 B2 * 4/2024 Meguro ................ G06V 10/56
(Continued)

FOREIGN PATENT DOCUMENTS

JP 2019-042157 A 3/2019
JP 2019-111040 A 7/2019
(Continued)

OTHER PUBLICATIONS

An Office Action; "Notice of Reasons for Refusal," mailed by the Japanese Patent Office on Aug. 16, 2022, which corresponds to Japanese Patent Application No. 2021-554199 and is related to U.S. Appl. No. 17/723,525; with English language translation.
(Continued)

*Primary Examiner* — Haris Sabah
(74) *Attorney, Agent, or Firm* — Studebaker & Brackett PC

(57) ABSTRACT

An image processing device includes a processor, and the processor decides whether or not to perform image processing on the medical image on the basis of an imaging condition of the medical image and/or an image analysis result obtained by analyzing the medical image. The processor performs, for the medical image on which the processor has decided to perform the image processing, at least one of calculation of an index value related to a stage of ulcerative colitis, determination of the stage of the ulcerative colitis, or determination of remission or non-remission of the ulcerative colitis on the basis of denseness of superficial blood vessels, intramucosal hemorrhage, and extramucosal hemorrhage that are obtained from the medical image.

12 Claims, 26 Drawing Sheets

(56) References Cited

U.S. PATENT DOCUMENTS

| | | | |
|---|---|---|---|
| 2014/0028821 A1 | 1/2014 | Tanaka et al. | |
| 2019/0073769 A1 | 3/2019 | Watanabe | |
| 2019/0204069 A1 | 7/2019 | Tatsuta et al. | |
| 2019/0380617 A1 | 12/2019 | Oosake et al. | |
| 2020/0242764 A1 | 7/2020 | Aoyama | |
| 2022/0039743 A1* | 2/2022 | Meguro | G06V 10/143 |

FOREIGN PATENT DOCUMENTS

| | | |
|---|---|---|
| WO | 2013/140667 A1 | 9/2013 |
| WO | 2018/051680 A1 | 3/2018 |
| WO | 2018/159461 A1 | 9/2018 |
| WO | 2019/078204 A1 | 4/2019 |

OTHER PUBLICATIONS

International Search Report issued in PCT/JP2020/036674; mailed Nov. 24, 2020.
International Preliminary Report on Patentability and Written Opinion issued in PCT/JP2020/036674; issued Apr. 26, 2022.

* cited by examiner

→ AREA OF HALATION REGION
Area (Signal ≥ S)

→ AREA OF HALATION REGION
Area (Signal ≥ S)

AREA OF HOOD
→ SHADOW REGION
SH1

AREA OF HOOD
→ SHADOW REGION
SH2

IMAGE PROCESSING DEVICE CAPABLE OF ACCURATELY DETERMINING ULCERATIVE COLITIS BY USING A MEDICAL IMAGE AND METHOD OF OPERATING THE SAME

CROSS-REFERENCE TO RELATED APPLICATIONS

This application is a Continuation of PCT International Application No. PCT/JP2020/036674 filed on 28 Sep. 2020, which claims priority under 35 U.S.C § 119(a) to Japanese Patent Application No. 2019-193042 filed on 23 Oct. 2019. The above application is hereby expressly incorporated by reference, in its entirety, into the present application.

BACKGROUND OF THE INVENTION

1. Field of the Invention

The present invention relates to an image processing device that performs processing related to a disease and a method of operating the same.

2. Description of the Related Art

In the medical field, a medical image has been widely used for diagnosis. For example, there is an endoscope system that comprises a light source device, an endoscope, and a processor device, as an apparatus using the medical image. In the endoscope system, an object to be observed is irradiated with illumination light and an image of the object to be observed illuminated with the illumination light is picked up, thereby acquiring an endoscopic image as the medical image. The endoscopic image is displayed on a monitor and used for diagnosis.

In recent years, processing has been performed on the basis of an endoscopic image, so that information for supporting diagnosis, for example, the determination of an abnormal region, such as a lesion part, has also been provided to a user. In addition, computer-aided diagnosis (CAD) technology has been developed in which an endoscopic image is subjected to appropriate image processing and the stage of a disease is determined, for example. In the CAD technology, it is desirable to perform image processing on the basis of a high-resolution endoscopic image in order to determine the stage with high accuracy.

For example, JP2019-111040A discloses an image analysis device that determines whether an image is a super-enlarged image which is an image to be analyzed by using a halation region included in the image, in a case where the state of the epithelium is analyzed by using an endoscope having a super-magnification function.

SUMMARY OF THE INVENTION

Incidentally, ulcerative colitis (UC) is known as one of the diseases of the large intestine. In a case where the distance from a distal end portion of an endoscope to an object to be observed, such as the mucosa of the large intestine, is long when ulcerative colitis is determined by endoscopic diagnosis, the resolution of an endoscopic image to be obtained is low, and it is difficult to accurately grasp biological properties, such as the shape of blood vessels and the presence or absence of hemorrhage, which are the base of stage determination. For example, in order to accurately make stage determination using the endoscopic image, it is necessary for a doctor to perform endoscopy again and to acquire an endoscopic image in which the distance to the object to be observed is appropriate again in a case where the distance to the object to be observed is long in the endoscopic image.

An object of the present invention is to provide an image processing device capable of accurately determining ulcerative colitis by using a medical image and a method of operating the same.

There is provided an image processing device according to an aspect of the present invention comprising: a processor, in which the processor acquires a medical image obtained by picking up an image of an object to be observed, decides whether or not to perform image processing on the medical image on the basis of an imaging condition of the medical image and/or an image analysis result obtained by analyzing the medical image, and performs, for the medical image on which the processor has decided to perform the image processing, at least one of calculation of an index value related to a stage of ulcerative colitis, determination of the stage of the ulcerative colitis, or determination of remission or non-remission of the ulcerative colitis on the basis of denseness of superficial blood vessels, intramucosal hemorrhage, and extramucosal hemorrhage that are obtained from the medical image.

It is preferable that the imaging condition of the medical image is a magnification ratio index of the medical image.

It is preferable that the image analysis result is at least one of a halation distribution, a frequency characteristic, a brightness value, or a shadow distribution that is obtained from the medical image.

It is preferable that the medical image is obtained by picking up the image of the object to be observed irradiated with auxiliary measurement light which is used to measure the object to be observed, and that the image analysis result is a position of an auxiliary measurement light irradiation region formed on the object to be observed in the medical image.

It is preferable that the processor performs, for the medical image on which the processor has decided to perform the image processing, at least one of the calculation of the index value related to the stage of the ulcerative colitis, the determination of the stage of the ulcerative colitis, or the determination of the remission or non-remission of the ulcerative colitis on the basis of the imaging condition of the medical image and/or the image analysis result obtained by analyzing the medical image.

It is preferable that, in a case where the processor determines the remission or non-remission of the ulcerative colitis, the processor classifies the denseness of the superficial blood vessels, the intramucosal hemorrhage, and the extramucosal hemorrhage depending on a frequency characteristic or a brightness value that is obtained from the medical image and determines the remission or non-remission of the ulcerative colitis according to the classification.

It is preferable that, in a case where the processor determines the remission or non-remission of the ulcerative colitis, the processor calculates a spatial frequency component distribution from the medical image, extracts a first frequency characteristic region having a first frequency characteristic, extracts a second frequency characteristic region having a second frequency characteristic of which a frequency is higher than a frequency of the first frequency characteristic, and extracts a third frequency characteristic region having a third frequency characteristic of which a frequency is higher than the frequency of the second frequency characteristic, on the basis of the spatial frequency component distribution, detects the denseness of the superficial blood vessels, the intramucosal hemorrhage, and the extramucosal hemorrhage on the basis of the first frequency characteristic region that is subjected to first region discrimination processing using a brightness value, the second frequency characteristic region that is subjected to second region discrimination processing using a brightness value, and the third frequency characteristic region, and determines the remission or non-remission of the ulcerative colitis on the basis of the denseness of the superficial blood vessels, the intramucosal hemorrhage, and the extramucosal hemorrhage.

It is preferable that the medical image is obtained by picking up the image of the object to be observed illuminated with illumination light including short-wavelength light. In addition, it is preferable that the illumination light is violet light of which a central wavelength or a peak wavelength includes a wavelength of 410 nm.

Further, there is provided a method of operating an image processing device according to another aspect of the present invention, the image processing device including a processor, the method comprising: an image acquisition step of, by the processor, acquiring a medical image obtained by picking up an image of an object to be observed; an image processing decision step of, by the processor, deciding whether or not to perform image processing on the medical image on the basis of an imaging condition of the medical image or an image analysis result obtained by analyzing the medical image; and a determination step of, by the processor, performing, for the medical image on which the processor has decided to perform the image processing, at least one of calculation of an index value related to a stage of ulcerative colitis, determination of the stage of the ulcerative colitis, or determination of remission or non-remission of the ulcerative colitis on the basis of denseness of superficial blood vessels, intramucosal hemorrhage, and extramucosal hemorrhage that are obtained from the medical image.

It is preferable that, in a case where the remission or non-remission of the ulcerative colitis is determined by the processor in the determination step, the determination step has a step of, by the processor, calculating a spatial frequency component distribution from the medical image, a step of, by the processor, extracting a first frequency characteristic region having a first frequency characteristic, extracting a second frequency characteristic region having a second frequency characteristic of which a frequency is higher than a frequency of the first frequency characteristic, and extracting a third frequency characteristic region having a third frequency characteristic of which a frequency is higher than the frequency of the second frequency characteristic, on the basis of the spatial frequency component distribution, a step of, by the processor, detecting the denseness of the superficial blood vessels, the intramucosal hemorrhage, and the extramucosal hemorrhage on the basis of the first frequency characteristic region that is subjected to first region discrimination processing using a brightness value, the second frequency characteristic region that is subjected to second region discrimination processing using a brightness value, and the third frequency characteristic region, and a step of, by the processor, determining the remission or non-remission of the ulcerative colitis on the basis of the denseness of the superficial blood vessels, the intramucosal hemorrhage, and the extramucosal hemorrhage. In addition, it is preferable that the medical image is obtained by picking up the image of the object to be observed illuminated with illumination light that is violet light of which a central wavelength or a peak wavelength includes a wavelength of 410 nm.

According to the present invention, it is possible to accurately determine ulcerative colitis by using medical images.

BRIEF DESCRIPTION OF THE DRAWINGS

FIGS. 8A and 8B are image views of a monitor that displays a special image, in which FIG. 8A is an image view of a special image 91a, and FIG. 8B is an image view of a special image 95a.

FIGS. 9A and 9B are views illustrating a halation distribution image, in which FIG. 9A is a view illustrating a case where a halation region is not included, and FIG. 9B is a view illustrating a case where a halation region is included.

FIGS. 10A and 10B are views illustrating a spatial frequency distribution image, in which FIG. 10A is a view illustrating a case where a low frequency region is included, and FIG. 10B is a view illustrating a case where a low frequency region is not included.

FIGS. 11A and 11B are views illustrating an average brightness value, in which FIG. 11A is a view illustrating the case of the special image 91a, and FIG. 11B is a view illustrating the case of the special image 95a.

FIGS. 12A and 12B are views illustrating a hood shadow region, in which FIG. 12A is a view illustrating the case of the special image 91a, and FIG. 12B is a view illustrating the case of the special image 95a.

FIGS. 15A and 15B are views illustrating a special image including a spot SP, in which FIG. 15A is a view illustrating the case of a special image 100a, and FIG. 15B is a view illustrating the case of a special image 100b.

DESCRIPTION OF THE PREFERRED EMBODIMENTS

First Embodiment

Figure 1:
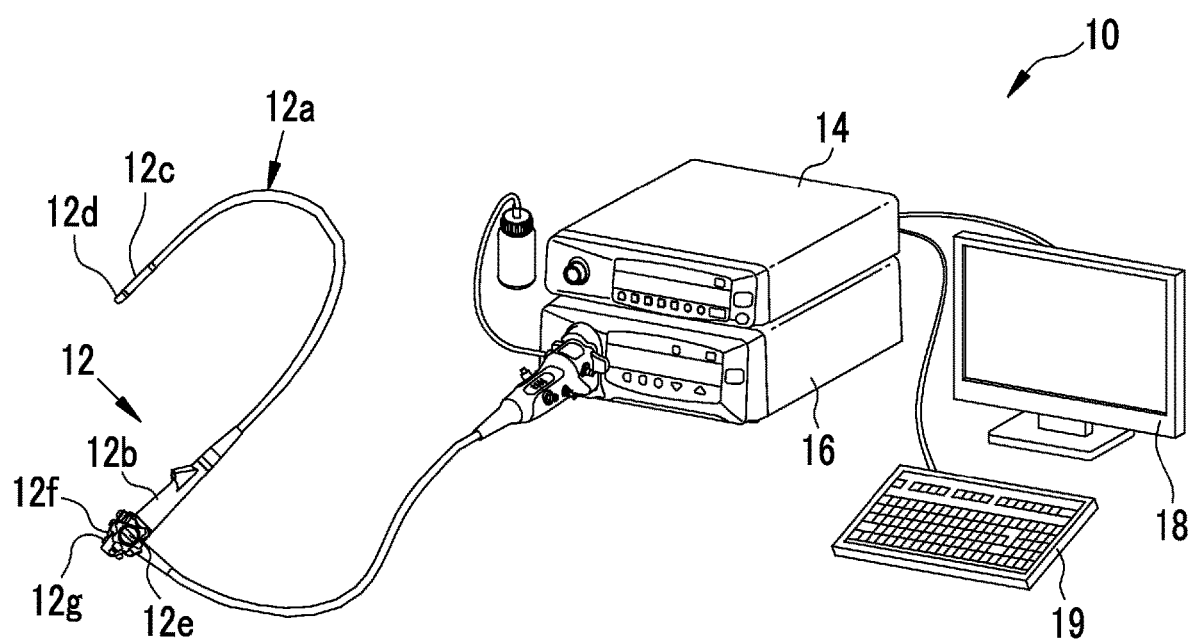
FIG. 1 is an external view of an endoscope system.

In FIG. 1, an endoscope system 10 includes an endoscope 12, a light source device 14, a processor device 16, a monitor 18, and a console 19. The endoscope 12 is optically connected to the light source device 14 and is electrically connected to the processor device 16. The endoscope 12 includes an insertion part 12a that is inserted into the body of an object to be observed, an operation part 12b that is provided at the proximal end portion of the insertion part 12a, and a bendable portion 12c and a distal end portion 12d that are provided on the distal end side of the insertion part 12a. An angle knob 12e of the operation part 12b is operated, whereby the bendable portion 12c is operated to be bent. As the bendable portion 12c is operated to be bent, the distal end portion 12d is made to face in a desired direction.

Further, the operation part 12b is provided with a mode changeover switch (SW) 12f that is used for an operation for switching a mode and a zoom operation portion 12g that provides an instruction to magnify/reduce an endoscopic image, in addition to the angle knob 12e.

The endoscope system 10 has three modes, that is, a normal light mode, a special light mode, and a disease-related processing mode. In the normal light mode, the object to be observed is illuminated with normal light and the image of the object to be observed is picked up, whereby a normal image having a natural hue is displayed on the monitor 18. In the special light mode, the object to be observed is illuminated with special light having a wavelength range different from the wavelength range of normal light and the image of the object to be observed is picked up, whereby a special image in which a specific structure is enhanced is displayed on the monitor 18. In the disease-related processing mode, the remission or non-remission of ulcerative colitis, which is one of diseases, is determined on the basis of the normal image or the special image. In the disease-related processing mode, an index value related to the stage of ulcerative colitis may be calculated or the stage of ulcerative colitis may be determined.

In the present embodiment, the special image (endoscopic image) is used in the disease-related processing mode, but the normal image may be used. Further, medical images, such as a radiographic image obtained from a radiographic device, a CT image obtained from computed tomography (CT), and an MRI image obtained from magnetic resonance imaging (MRI), may be used as an image that is used in the disease-related processing mode, in addition to the special image as an endoscopic image that is one of medical images. Furthermore, the disease-related processing mode is executed in the processor device 16 to which the endoscope 12 is connected, but the disease-related processing mode may be executed by other methods. For example, an external image processing device separate from the endoscope system 10 may be provided with the function of a disease-related processing unit 66 (FIG. 2), a medical image may be input to the external image processing device and then the disease-related processing mode may be executed, and the execution result of the disease-related processing mode may be displayed on an external monitor connected to the external image processing device.

The processor device 16 is electrically connected to the monitor 18 and the console 19. The monitor 18 outputs and displays the image of the object to be observed, information incidental to the image of the object to be observed, and the like. The console 19 functions as a user interface that receives an input operation, such as function settings. An external recording unit (not shown) that records images, image information, and the like may be connected to the processor device 16. Further, the processor device 16 corresponds to an image processing device according to the embodiment of the invention.

Figure 2:
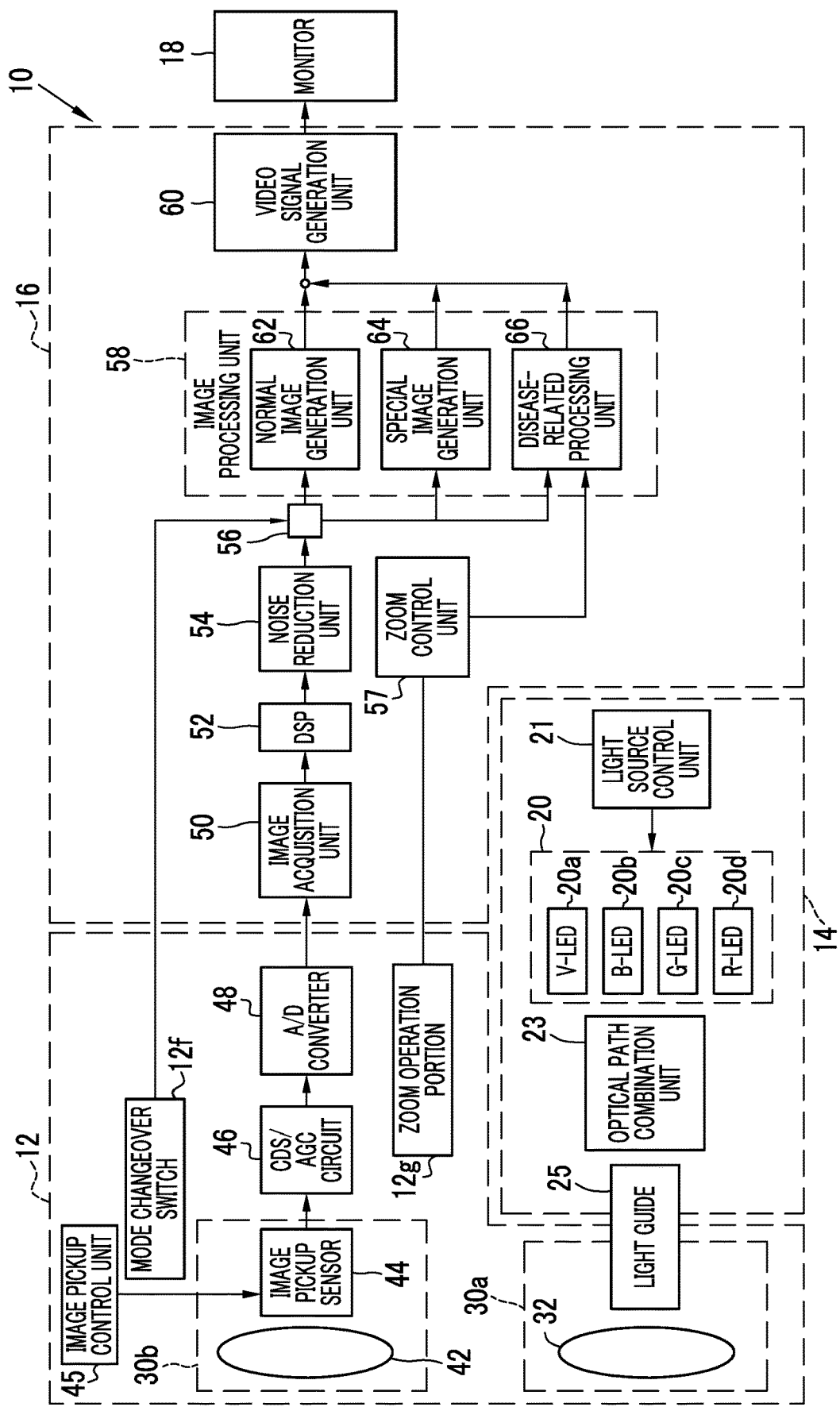
FIG. 2 is a block diagram showing the functions of the endoscope system of a first embodiment.

In FIG. 2, the light source device 14 comprises a light source unit 20 and a light source control unit 21 that controls the light source unit 20. The light source unit 20 includes, for example, a plurality of semiconductor light sources, turns on or off each of these semiconductor light sources, and controls the amount of emitted light to emit illumination light with which the object to be observed is illuminated, in a case where the light source unit 20 turns on each semiconductor light source. In the present embodiment, the light source unit 20 includes four-color LEDs, that is, a violet light emitting diode (V-LED) 20a, a blue light emitting diode (B-LED) 20b, a green light emitting diode (G-LED) 20c, and a red light emitting diode (R-LED) 20d.

Figure 3:
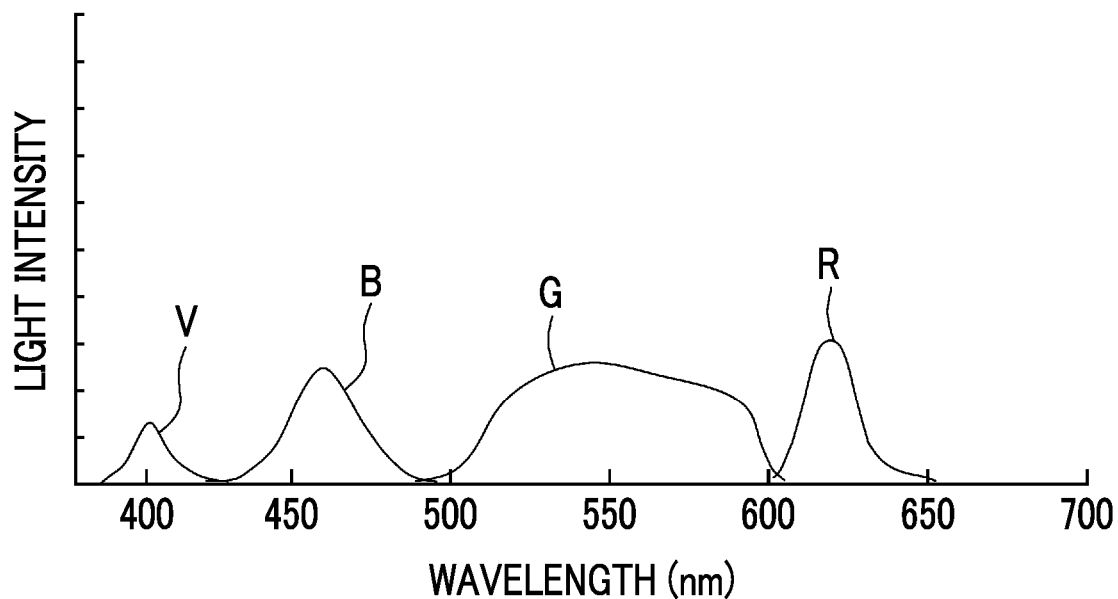
FIG. 3 is a graph showing the spectra of violet light V, blue light B, green light G, and red light R.

As shown in FIG. 3, the V-LED 20a generates violet light V having a central wavelength of 405±10 nm and a wavelength range of 380 to 420 nm. The B-LED 20b generates blue light B having a central wavelength of 460±10 nm and a wavelength range of 420 to 500 nm. The G-LED 20c generates green light G having a wavelength range of 480 to 600 nm. The R-LED 20d generates red light R having a central wavelength of 620 to 630 nm and a wavelength range of 600 to 650 nm. Violet light V is short-wavelength light that is used to detect the denseness of superficial blood vessels, intramucosal hemorrhage, and extramucosal hemorrhage used in the disease-related processing mode, and it is preferable that the central wavelength or the peak wavelength of the violet light V includes a wavelength of 410 nm.

The light source control unit 21 controls the V-LED 20a, the B-LED 20b, the G-LED 20c, and the R-LED 20d. Further, the light source control unit 21 controls the respective LEDs 20a to 20d so that normal light of which the light intensity ratios of violet light V, blue light B, green light G, and red light R are Vc:Bc:Gc:Rc is emitted in the normal light mode.

Figure 4:
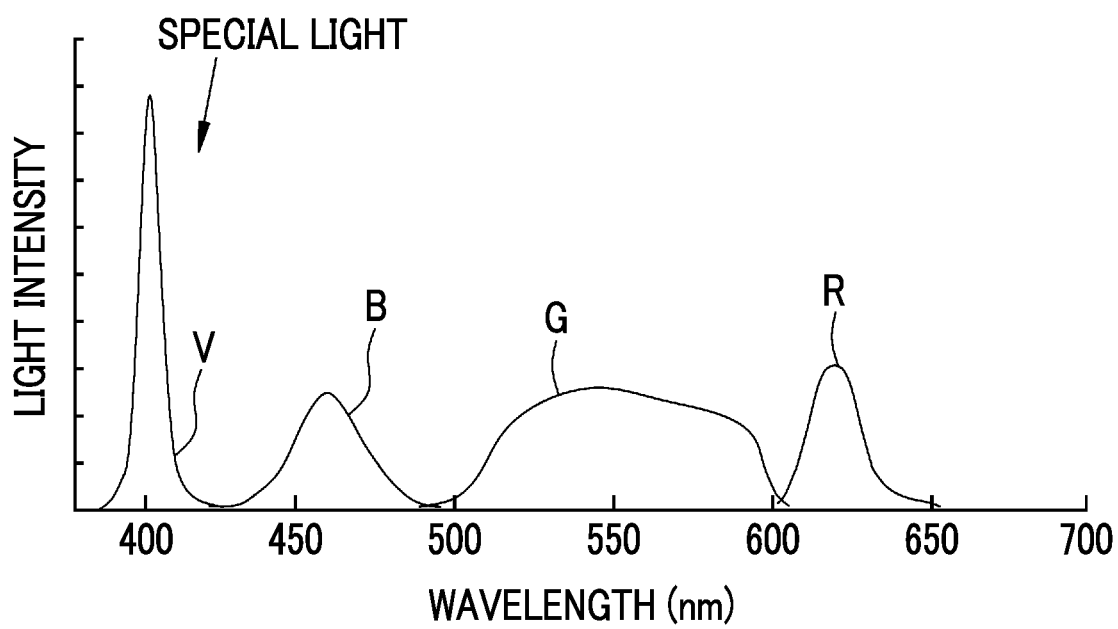
FIG. 4 is a graph showing the spectrum of special light of the first embodiment.
Figure 5:
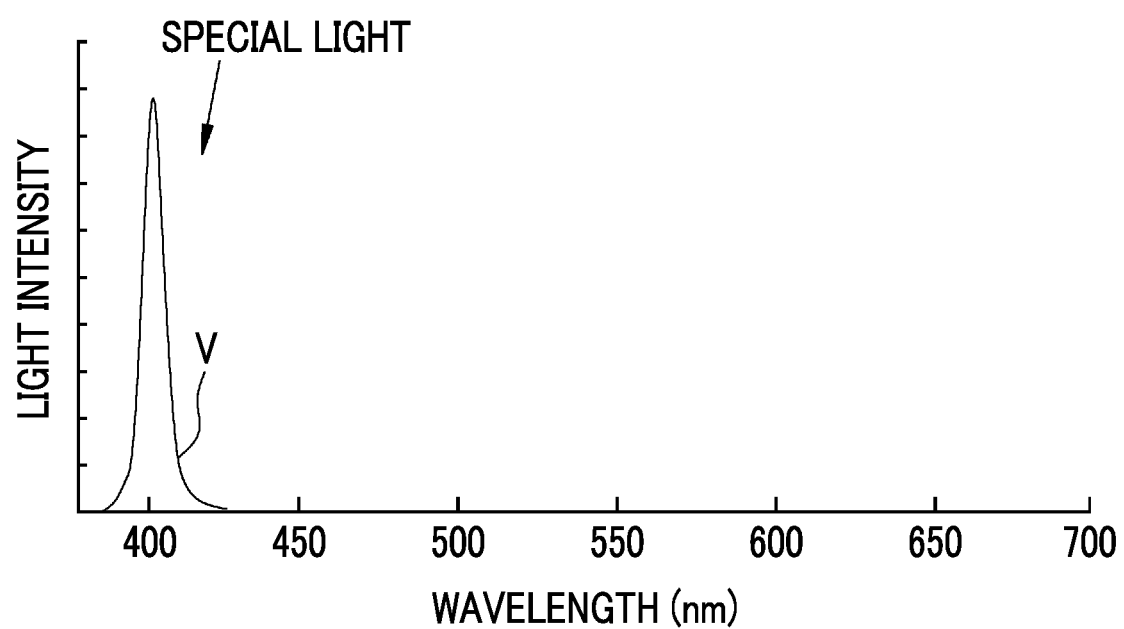
FIG. 5 is a graph showing the spectrum of special light that includes only violet light V.

Furthermore, the light source control unit 21 controls the respective LEDs 20a to 20d so that special light of which the light intensity ratios of violet light V as short-wavelength light, blue light B, green light G, and red light R are Vs:Bs:Gs:Rs is emitted in the special light mode or the disease-related processing mode. It is preferable that special light of which the light intensity ratios are Vs:Bs:Gs:Rs enhances superficial blood vessels and the like. For this reason, it is preferable that the light intensity of violet light V of the special light is set to be higher than the light intensity of blue light B. For example, as shown in FIG. 4, a ratio of the light intensity Vs of violet light V to the light intensity Bs of blue light B is set to "4:1". Alternatively, as shown in FIG. 5, with regard to special light, the light intensity ratios of violet light V, blue light B, green light G, and red light R are set to 1:0:0:0 and only violet light V as short-wavelength light may be emitted.

In the present specification, the light intensity ratios include a case where the ratio of at least one semiconductor light source is 0 (zero). Accordingly, the light intensity ratios include a case where any one or two or more of the respective semiconductor light sources are not turned on. For example, the light source unit 20 is regarded to have light intensity ratios even when only one semiconductor light source is turned on and the other three semiconductor light sources are not turned on as in a case where the light intensity ratios of violet light V, blue light B, green light G, and red light R are 1:0:0:0.

Light emitted from each of the LEDs 20a to 20d is incident on a light guide 25 through an optical path combination unit 23 that is constituted of a mirror, a lens, and the like. The light guide 25 is built in the endoscope 12 and a universal cord (a cord that connects the endoscope 12 to the light source device 14 and the processor device 16). The light guide 25 propagates light from the optical path combination unit 23 to the distal end portion 12d of the endoscope 12.

The distal end portion 12d of the endoscope 12 is provided with an illumination optical system 30a and an image pickup optical system 30b. The illumination optical system 30a includes an illumination lens 32, and the object to be observed is irradiated with illumination light propagated by the light guide 25, through the illumination lens 32. The image pickup optical system 30b includes an objective lens 42 and an image pickup sensor 44. Light from the object to be observed caused by the irradiation with the illumination light is incident on the image pickup sensor 44, through the objective lens 42. With this, the image of the object to be observed is formed on the image pickup sensor 44.

A charge coupled device (CCD) image pickup sensor or a complementary metal-oxide semiconductor (CMOS) image pickup sensor can be used as the image pickup sensor 44. Further, a complementary color image pickup sensor that comprises complementary color filters of cyan (C), magenta (M), yellow (Y), and green (G) may be used instead of the primary color image pickup sensor 44. In a case where a complementary color image pickup sensor is used, image signals of four colors of C, M, Y, and G are output. Therefore, the image signals of four colors of C, M, Y, and G are converted into image signals of three colors of R, G, and B by complementary color-primary color conversion, so that image signals of the same respective colors of R, G, and B as those of the image pickup sensor 44 can be obtained.

The image pickup sensor 44 is driven and controlled by the image pickup control unit 45. The control performed by the image pickup control unit 45 differs depending on the respective modes. In the normal light mode or the disease-related processing mode, the image pickup control unit 45 controls the image pickup sensor 44 such that the image pickup sensor 44 picks up the image of the object to be observed illuminated with normal light. With this, Bc image signals are output from the B pixels of the image pickup sensor 44, Gc image signals are output from the G pixels thereof, and Rc image signals are output from the R pixels thereof.

In the special light mode or the disease-related processing mode, the image pickup control unit 45 controls the image pickup sensor 44 such that the image pickup sensor 44 picks up the image of the object to be observed illuminated with special light. With this, Bs image signals are output from the B pixels of the image pickup sensor 44, Gs image signals are output from the G pixels thereof, and Rs image signals are output from the R pixels thereof.

A correlated double sampling/automatic gain control (CDS/AGC) circuit 46 performs correlated double sampling (CDS) or automatic gain control (AGC) on the analog image signals that are obtained from the image pickup sensor 44. The image signals that have been passed through the CDS/AGC circuit 46 are converted into digital image signals by an analog/digital (A/D) converter 48. The digital image signals that have been subjected to A/D conversion are input to the processor device 16.

The processor device 16 comprises an image acquisition unit 50, a digital signal processor (DSP) 52, a noise reduction unit 54, an image processing switching unit 56, an image processing unit 58, and a video signal generation unit 60. The image processing unit 58 comprises a normal image generation unit 62, a special image generation unit 64, and a disease-related processing unit 66.

The image acquisition unit 50 acquires the image signals of an endoscopic image that is one of medical images input from the endoscope 12. The acquired image signals are transmitted to the DSP 52. The DSP 52 performs various types of signal processing, such as defect correction processing, offset processing, gain correction processing, linear matrix processing, gamma conversion processing, demosaicing processing, and YC conversion processing, on the received image signals. In the defect correction processing, signals of defective pixels of the image pickup sensor 44 are corrected. In the offset processing, dark current components are removed from the image signals that have been subjected to the defect correction processing, so that an accurate zero level is set. In the gain correction processing, the image signals of each color, which have been subjected to the offset processing, are multiplied by a specific gain, so that the signal level of each image signal is adjusted. The image signals of each color, which have been subjected to the gain correction processing, are subjected to the linear matrix processing for improving color reproducibility.

After that, the brightness or chroma saturation of each image signal is adjusted by the gamma conversion processing. The image signals that have been subjected to the linear matrix processing are subjected to the demosaicing processing (also referred to as equalization processing or demosaicing), so that signals of colors missed in the respective pixels are generated by interpolation. All the pixels are made to have signals of the respective colors of R, G, and B by the demosaicing processing. The DSP 52 performs the YC conversion processing on the respective image signals that have been subjected to the demosaicing processing, and outputs brightness signals Y, color difference signals Cb, and color difference signals Cr to the noise reduction unit 54.

The noise reduction unit 54 performs noise reduction processing, which is performed using, for example, a moving average method or median filtering, on the image signals that have been subjected to the demosaicing processing and the like by the DSP 52. The image signals from which noise has been reduced are input to the image processing switching unit 56.

The image processing switching unit 56 switches a destination to which the image signals from the noise reduction unit 54 are transmitted to any one of the normal image generation unit 62, the special image generation unit 64, or the disease-related processing unit 66, in response to the set mode. Specifically, in a case where, for example, the normal light mode is set, the image signals from the noise reduction unit 54 are input to the normal image generation unit 62. In a case where the special light mode is set, the image signals from the noise reduction unit 54 are input to the special image generation unit 64. In a case where the disease-related processing mode is set, the image signals from the noise reduction unit 54 are input to the disease-related processing unit 66.

The normal image generation unit 62 performs image processing for a normal image on the input Rc image signals, Gc image signals, and Bc image signals corresponding to one frame. The image processing for a normal image includes color conversion processing, such as 3×3 matrix processing, gradation transformation processing, and three-dimensional look up table (LUT) processing, color enhancement processing, and structure enhancement processing, such as spatial frequency enhancement. The Rc image signals, the Gc image signals, and the Bc image signals that have been subjected to the image processing for a normal image are input to the video signal generation unit 60 as a normal image.

The special image generation unit 64 performs image processing for a special image on the input Rs image signals, Gs image signals, and Bs image signals corresponding to one frame. The image processing for a special image includes color conversion processing, such as 3×3 matrix processing, gradation transformation processing, and three-dimensional look up table (LUT) processing, color enhancement processing, and structure enhancement processing, such as spatial frequency enhancement. The Rs image signals, the Gs image signals, and the Bs image signals that have been subjected to the image processing for a special image are input to the video signal generation unit 60 as a special image.

The disease-related processing unit 66 decides whether or not to perform image processing on the special image on the basis of the imaging condition of the special image or the image analysis result obtained by analyzing the special image. In this case, the disease-related processing unit 66 receives information regarding zooming based on the operation of the zoom operation portion 12g, through a zoom control unit 57. The disease-related processing unit 66 performs, for the special image on which the disease-related processing unit 66 has decided to perform the image processing, at least one of the calculation of an index value related to the stage of ulcerative colitis, the determination of the stage of ulcerative colitis, or the determination of the remission or non-remission of ulcerative colitis on the basis of the denseness of superficial blood vessels, intramucosal hemorrhage, and extramucosal hemorrhage obtained from the special image. Information regarding the determination result is input to the video signal generation unit 60. The details of the disease-related processing unit 66 will be described later. In the first to third embodiments, a case where the disease-related processing unit 66 determines the remission or non-remission of ulcerative colitis will be described.

The video signal generation unit 60 converts the normal image, the special image, or the information regarding the determination result, which is output from the image processing unit 58, into video signals that allow the monitor 18 to be displayed in full color. The video signals that have been converted are input to the monitor 18. With this, the normal image, the special image, or the information regarding the determination result is displayed on the monitor 18.

Figure 6:
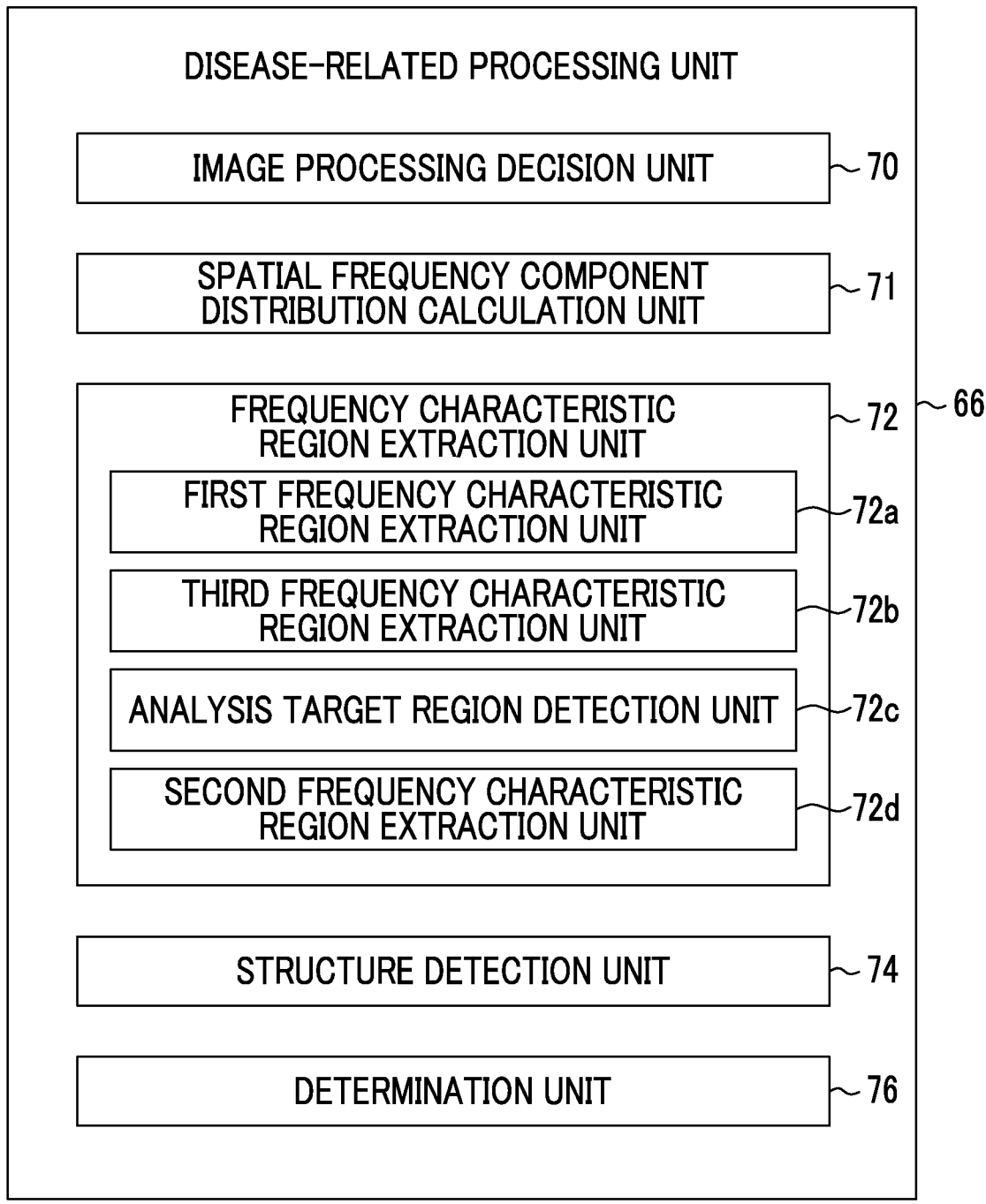
FIG. 6 is a block diagram showing the functions of a disease-related processing unit.

The details of the disease-related processing unit 66 will be described below. As shown in FIG. 6, the disease-related processing unit 66 comprises an image processing decision unit 70, a spatial frequency component distribution calculation unit 71, a frequency characteristic region extraction unit 72, a structure detection unit 74, and a determination unit 76. The image processing decision unit 70 decides whether or not to perform image processing on the special image on the basis of the imaging condition of the special image and/or the image analysis result obtained by analyzing the special image. The image processing is performed on the special image on which the image processing decision unit 70 has decided to perform the image processing. The spatial frequency component distribution calculation unit 71, the frequency characteristic region extraction unit 72, the structure detection unit 74, and the determination unit 76 perform image processing. The image processing will be described later.

Figure 7:
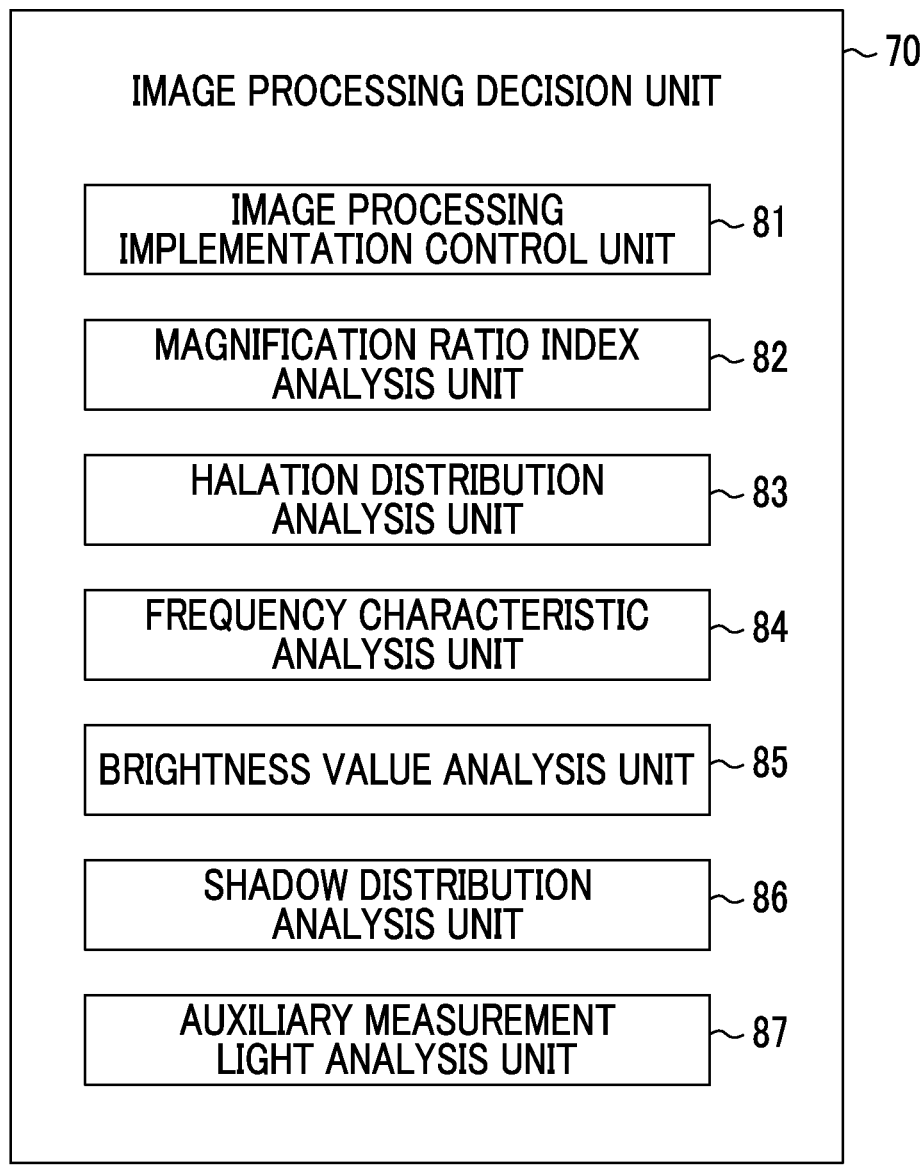
FIG. 7 is a block diagram showing the functions of an image processing decision unit.

The image processing decision unit 70 decides whether or not to perform image processing on the special image, which is a medical image, on the basis of the imaging condition of the special image and/or the image analysis result obtained by analyzing the special image. As shown in FIG. 7, the image processing decision unit 70 comprises an image processing implementation control unit 81, a magnification ratio index analysis unit 82, a halation distribution analysis unit 83, a frequency characteristic analysis unit 84, a brightness value analysis unit 85, a shadow distribution analysis unit 86, an auxiliary measurement light analysis unit 87.

The image processing implementation control unit 81 performs control related to the image processing decision unit 70. The control related to the image processing decision unit 70 includes control such as that which of the imaging condition of the special image and/or the image analysis result obtained by analyzing the special image is used to decide whether or not to perform image processing on the special image, and control of deciding whether or not to perform image processing on the special image after a plurality of image analysis results are integrated in a case where these analysis results are obtained. Which of the imaging condition of the special image and/or the image analysis result obtained by analyzing the special image is used to decide whether or not to perform image processing on the special image is set in advance. For example, after all the imaging condition and the image analysis result are obtained, the image processing implementation control unit 81 may integrate these analysis results and then decide whether or not to perform image processing, or may decide whether or not to perform image processing only by using the imaging condition.

Further, the image processing implementation control unit 81 performs control of sending the imaging condition of the special image and/or the image analysis result obtained by analyzing the special image to the disease-related processing unit 66. The disease-related processing unit performs, for the special image on which the image processing decision unit has decided to perform the image processing, at least one of the calculation of the index value related to the stage of ulcerative colitis, the determination of the stage of ulcerative colitis, or the determination of the remission or non-remission of ulcerative colitis by using the imaging condition of the special image and/or the image analysis result obtained by analyzing the special image sent from the image processing implementation control unit 81.

In a case where decision is made on the basis of the imaging condition of the special image, for example, a magnification ratio index is used. As the imaging condition, the imaging distance that is the distance between the object to be observed and the distal end portion of the endoscope, the amount of illumination light, or the like may be used in addition to the magnification ratio index. In a case where decision is made on the basis of the image analysis result obtained by analyzing the special image, for example, the halation distribution, the frequency characteristic, the brightness value, the shadow distribution, or the position of the auxiliary measurement light is used. The analysis result may be used alone or in combination of two or more. In a case where the analysis result is used in combination of two or more, the image processing implementation control unit 81 integrates these analysis results to decide whether or not to perform image processing in accordance with a preset standard.

The magnification ratio index used in a case where decision is made on the basis of the imaging condition is an index related to a magnification ratio. For example, information regarding the magnification ratio, such as the operation history of the zoom operation portion, the types of zoom, and the ratio of each zoom, in addition to the imaging condition in acquiring the special image, such as the magnification ratio using optical zoom and/or electronic zoom, the focal length, or depth of field, can be used. Further, information regarding the magnification ratio obtained by image analysis of the special image may be used. The magnification ratio is a relative value, and refers to a value indicating the ratio of the image size of the object to be observed included in an image obtained by image pickup with the operation such as magnification or zooming, for example, in a case where the image size of the object to be observed included in an image obtained by image pickup without the operation such as magnification or zooming is set as a reference.

In the present embodiment, optical zoom and electronic zoom are provided as the types of zoom. The optical zoom moves the lens and adjusts the focal length to magnify the image of the object to be observed, which is formed on the image pickup sensor, thereby magnifying the object to be observed displayed on the monitor. Further, the electronic zoom trims a part of the image signals (for example, the central part) obtained by picking up the image of the object to be observed and enlarges the trimmed range to make the monitor display the image, thereby magnifying the object to be observed. In the present embodiment, the type of zoom may be any one of optical zoom, electronic zoom, or both optical zoom and electronic zoom.

Figure 8A:
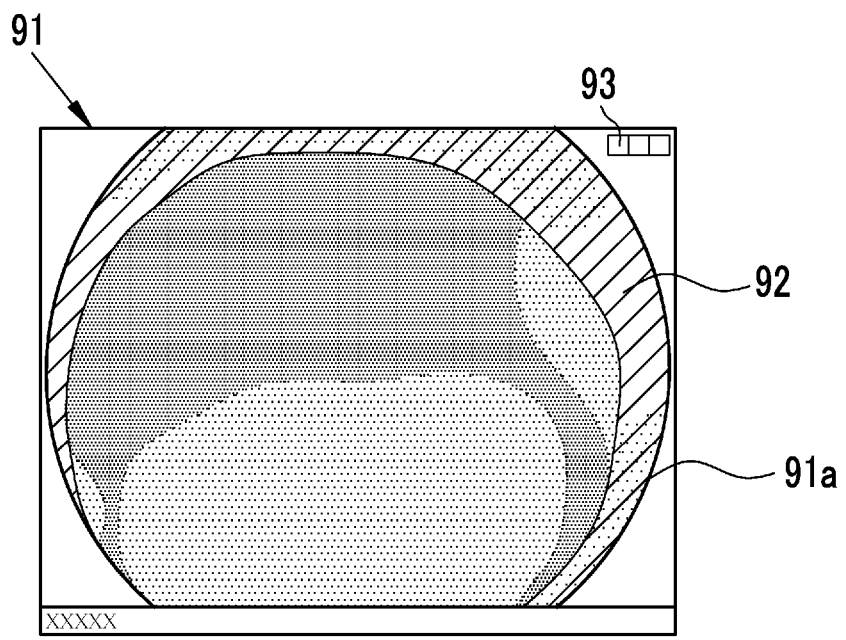
Figure 8B:
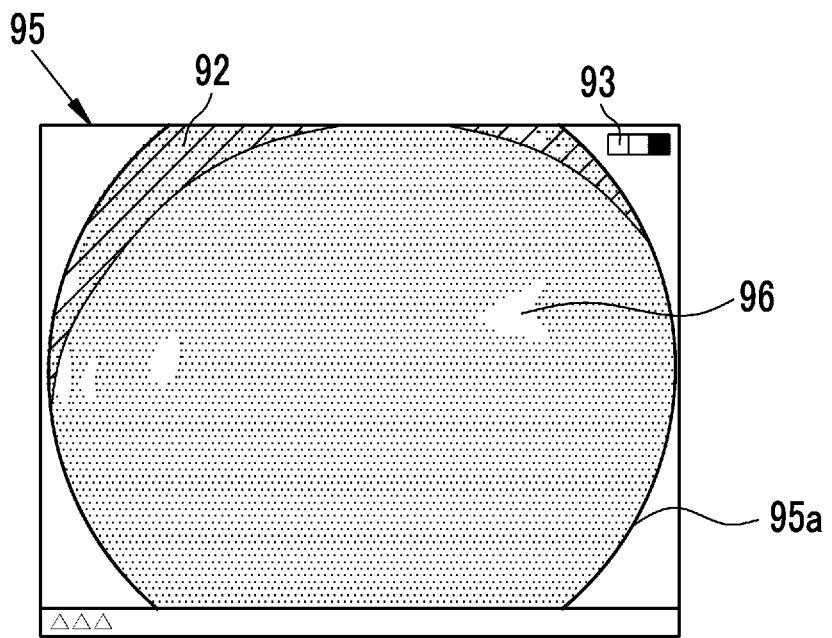

As shown in FIGS. 8A and 8B, in a case where the image of the object to be observed is displayed on the monitor, for example, a dark part exists because a hood 92 attached to the distal end portion 12*d* of the endoscope forms a shadow or the like in a special image 91*a* displayed on a monitor image 91 in which the operation such as magnification is not performed, as shown in FIG. 8A. Further, for example, as shown in FIG. 8B, in a special image 95*a* displayed on a monitor image 95 in which the magnification operation is performed, illumination light is transmitted through the transparent hood 92 and reaches the object to be observed, and a halation region 96 is formed. The hood 92 is shown by diagonal lines in FIGS. 8A and 8B, and FIGS. 11A, 11B, 12A, 12B, 22, and 23. Further, in the monitor images 91 and 95, a magnification ratio display 93 indicating the magnification ratio is shown so that a user can easily grasp the magnification ratio.

The magnification ratio index analysis unit 82 receives information regarding the magnification ratio index and the like from the zoom control unit 57 and the like, and calculates the magnification ratio by analyzing the information. The magnification ratio is sent to the image processing implementation control unit 81 in order to decide whether or not to perform image processing on the special image. The image processing implementation control unit 81 decides to perform the image processing in a case where the calculated magnification ratio is a preset threshold value or more, and decides not to perform the image processing in a case where the magnification ratio is less than the preset threshold value.

Next, in a case where decision is made on the basis of the image analysis result obtained by analyzing the special image, for example, the halation distribution, the frequency characteristic, the brightness value, the shadow distribution, or the position of the auxiliary measurement light can be used as the image analysis result. The halation distribution is a calculation of the distribution of the halation region included in the special image. The frequency characteristic is a calculation of the distribution of the spatial frequency component of the special image. The brightness value is a calculation of the brightness value of the special image. The shadow distribution is a calculation of the distribution of a shadow region in a case where the special image includes a shadow formed on the object to be observed by the hood provided at the distal end portion of the endoscope. The reflected light position of the auxiliary measurement light is a calculation of the position of a bright spot formed on the object to be observed by the auxiliary measurement light with which the object to be observed is irradiated in a case where the object to be observed is measured.

The halation distribution analysis unit 83 performs image analysis of the special image related to the halation distribution. In the special image, there is a case where a halation region having an extremely high brightness value as compared with the surroundings may be generated due to the distance between the distal end portion 12*d* of the endoscope and the object to be observed. The distance between the distal end portion 12*d* of the endoscope and the object to be observed is relatively short in a case where the special image includes the halation region, and the distance between the distal end portion 12*d* of the endoscope and the object to be observed is relatively long in a case where the special image does not include the halation region. Accordingly, the special image is analyzed and the distribution of the halation region is calculated, so that it is possible to obtain an index of the distance between the distal end portion 12*d* of the endoscope and the object to be observed or the resolution of the special image.

For example, as shown in FIG. 8B, the special image 95*a* includes a plurality of halation regions 96. In order to avoid the complexity of the figure, only a part of the halation regions is designated by a reference numeral in FIG. 8B. Further, since FIG. 8B is an image in which the magnification operation is performed, the magnification ratio display 93 indicates that this image is a special image in which magnification operation is performed.

Figure 9A:
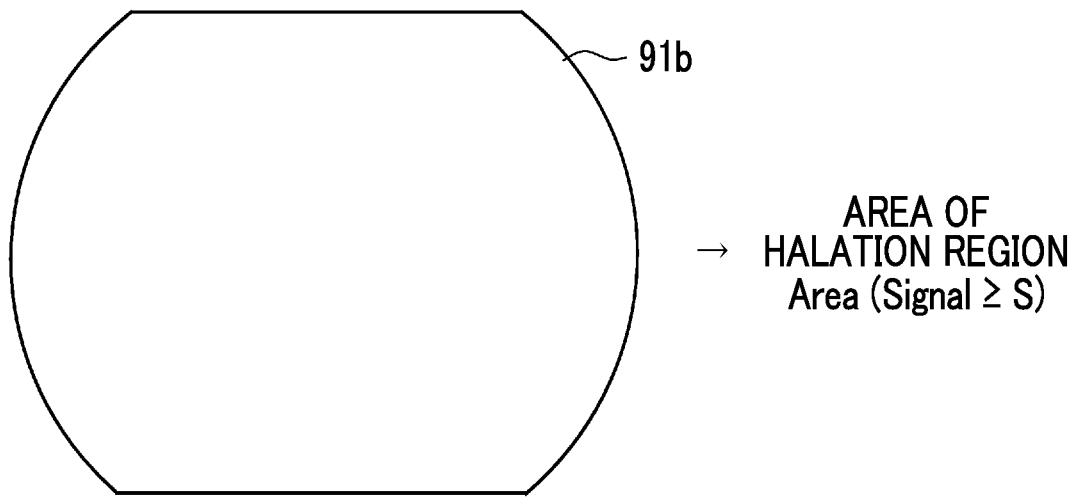
Figure 9B:
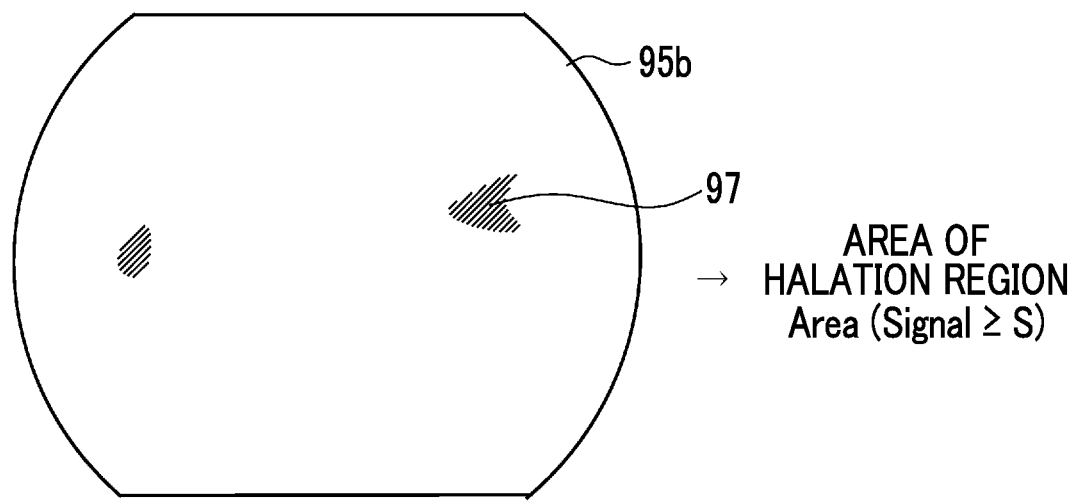

The halation distribution analysis unit 83 sets a region having a preset specific brightness value or more, as the halation region. For example, as shown in FIGS. 9A and 9B, in the special image, a halation distribution image showing the region having a preset specific brightness value or more is created. As shown in FIG. 9B, a high brightness region 97 that is a region (Signal≥S) having the specific brightness value (S) or more based on the halation region is formed in a halation distribution image 95b created on the basis of the special image 95a. Further, as shown in FIG. 9A, the high brightness region 97 is not formed in a halation distribution image 91b created on the basis of the special image 91a. The halation distribution analysis unit 83 calculates the area (Area (Signal≥S)) of the high brightness region 97 for each image on the basis of the halation distribution images 91b and 95b.

In the following figures including FIGS. 9A and 9B, the figure such as a special image schematically illustrates an image when displayed on a monitor, but the shape of the special image can be appropriately set depending on the case regardless of the shape of the actual special image or the like, and may be circular or rectangular.

The area of each high brightness region 97 in the halation distribution images 91b and 95b based on the special images 91a and 95a is sent to the image processing implementation control unit 81 in order to decide whether or not to perform image processing on the special images 91a and 95a. The image processing implementation control unit 81 decides to perform the image processing on the special image in a case where the calculated area of each high brightness region 97 is a preset threshold value or more, and decides not to perform the image processing on the special image in which the area of the high brightness region 97 is less than the preset threshold value.

The frequency characteristic analysis unit 84 performs image analysis of the special image related to the frequency characteristic. The spatial frequency distribution of the special image is calculated by the analysis. For example, the deep part of the lumen where the distance between the distal end portion 12d of the endoscope and the object to be observed is long and illumination light does not reach is a low frequency region where the spatial frequency is lower than the surroundings. Further, for example, a part where the distance between the distal end portion 12d of the endoscope and the object to be observed is short and illumination light reaches the entire object to be observed does not include the low frequency region. Accordingly, the analysis for calculating the spatial frequency distribution is performed for the special image, so that it is possible to obtain an index of the distance between the distal end portion 12d of the endoscope and the object to be observed or the resolution of the special image.

Figure 10A:
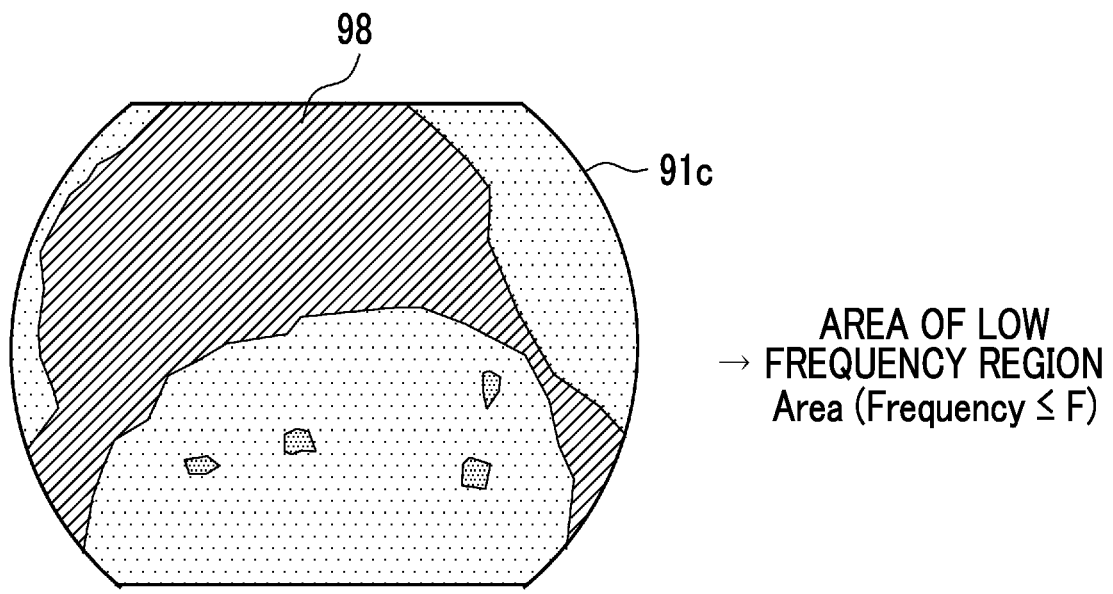
Figure 10B:
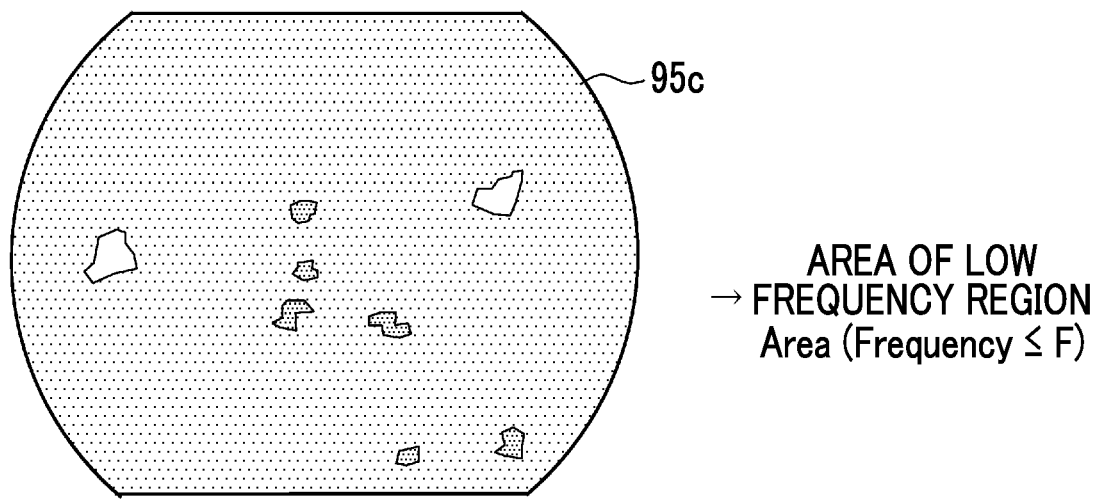

As shown in FIG. 10A, a spatial frequency distribution image 91c created on the basis of the special image 91a includes a low frequency region (Frequency≤F) 98 where the spatial frequency is lower than the surroundings. Further, as shown in FIG. 10B, a spatial frequency distribution image 95c created on the basis of the special image 95a does not include the low frequency region 98. The frequency characteristic analysis unit 84 calculates the area (Area (Frequency≤F)) of the low frequency region 98 for each image on the basis of the spatial frequency distribution images 91c and 95c.

The area of each low frequency region 98 in the spatial frequency distribution images 91c and 95c based on the special images 91a and 95a is sent to the image processing implementation control unit 81 in order to decide whether or not to perform image processing on the special images 91a and 95a. The image processing implementation control unit 81 decides to perform the image processing on the special image in a case where the calculated area of the low frequency region 98 is a preset threshold value or less, and decides not to perform the image processing on the special image in which the area of the low frequency region 98 is more than the preset threshold value.

The brightness value analysis unit 85 performs image analysis of the special image related to the brightness value. The brightness value distribution of the special image is calculated by the analysis. For example, the average brightness value of the entire special image is calculated on the basis of the brightness value distribution calculated on the basis of the special image. For example, in a case where the area of the deep part of the lumen where the distance between the distal end portion 12d of the endoscope and the object to be observed is long and illumination light does not reach is large, the average brightness value becomes small. Further, for example, the average brightness value of a part where the distance between the distal end portion 12d of the endoscope and the object to be observed is short and illumination light reaches the most part of the object to be observed becomes large. Accordingly, the analysis for calculating the brightness value is performed for the special image, so that it is possible to obtain an index of the distance between the distal end portion 12d of the endoscope and the object to be observed or the resolution of the special image.

Figure 11A:
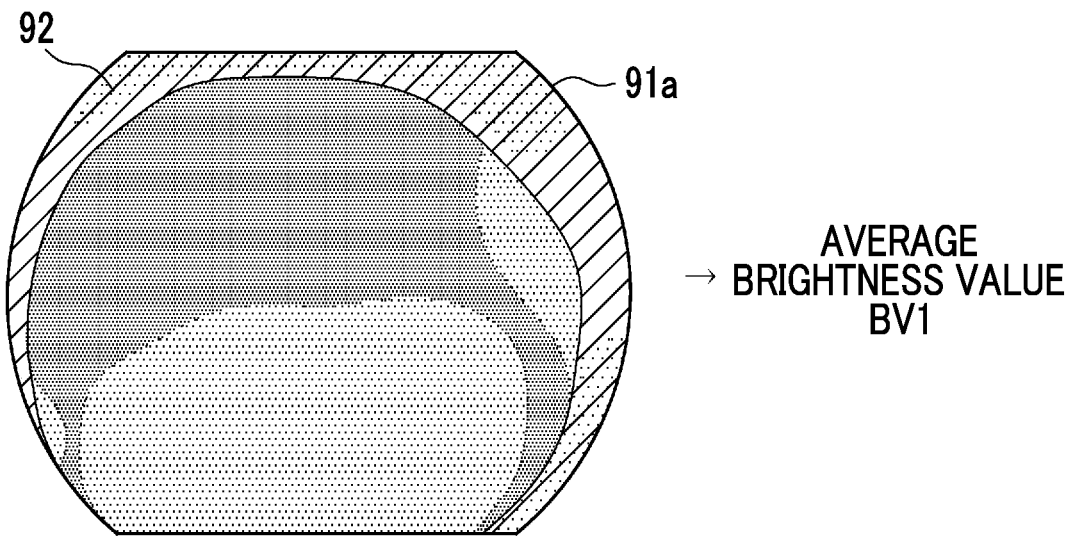
Figure 11B:
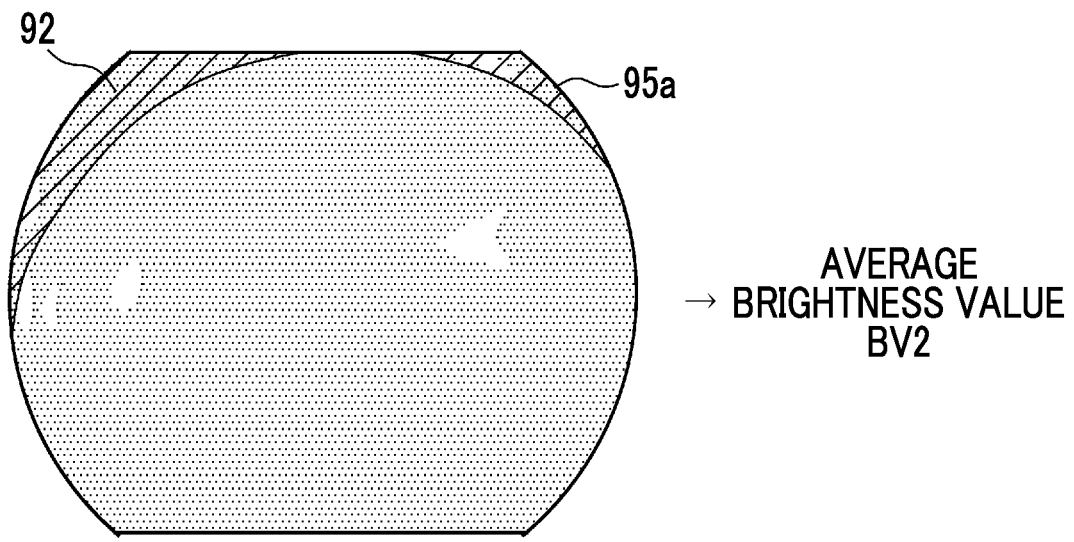

As shown in FIG. 11A, the brightness value analysis unit 85 calculates the brightness value distribution on the basis of the special image 91a, and calculates an average brightness value BV1 for the entire image of the special image 91a from the brightness value distribution. Further, as shown in FIG. 11B, the brightness value analysis unit 85 calculates the brightness value distribution on the basis of the special image 95a, and calculates an average brightness value BV2 for the entire image of the special image 95a from the brightness value distribution.

The average brightness values BV1 and BV2 in the special images 91a and 95a are each sent to the image processing implementation control unit 81 in order to decide whether or not to perform image processing on the special images 91a and 95a. The image processing implementation control unit 81 decides to perform the image processing on the special image in a case where the calculated average brightness value is a preset threshold value or more, and decides not to perform the image processing on the special image in which the average brightness value is less than the preset threshold value.

The shadow distribution analysis unit 86 performs image analysis of the special image related to a shadow (hereinafter, referred to as a hood shadow) generated on the object to be observed due to the hood attached to the distal end portion 12d of the endoscope. The distribution of the region of the hood shadow included in the special image (hereinafter, referred to as a hood shadow region) is calculated by the analysis. For example, in a case where the distance between the distal end portion 12d of the endoscope and the object to be observed is long, the hood shadow region becomes large because the angle of illumination light with respect to the object to be observed is separated from the vertical. Further, for example, in a case where the distance between the distal end portion 12d of the endoscope and the object to be observed is short, the hood shadow region becomes small because the angle of illumination light with respect to the object to be observed is close to the vertical. Accordingly, the analysis for calculating the distribution of the hood shadow region is performed for the special image, so that it is possible to obtain an index of the distance between the distal end portion 12d of the endoscope and the object to be observed or the resolution of the special image.

Figure 12A:
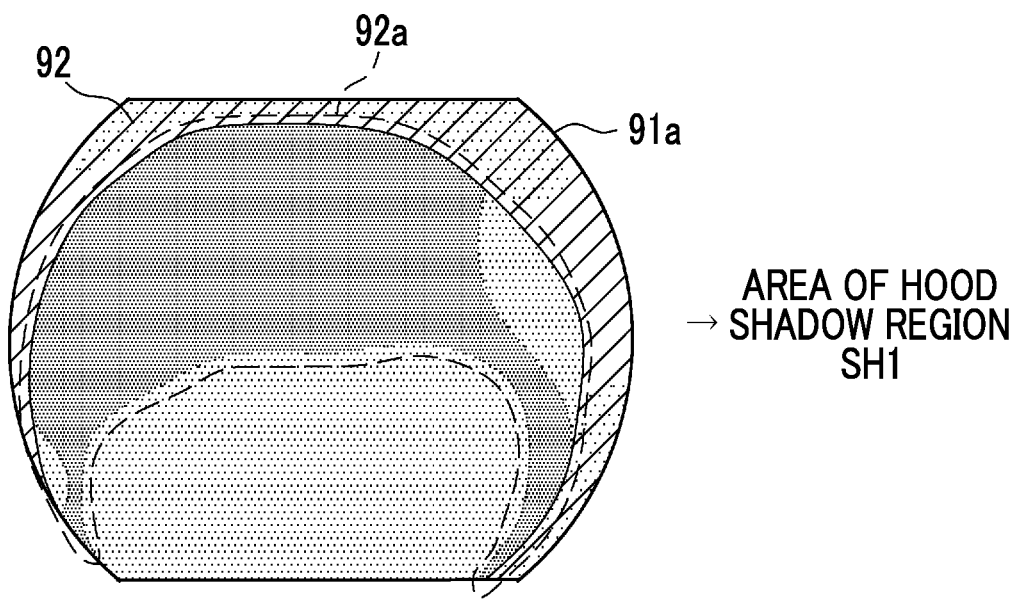
Figure 12B:
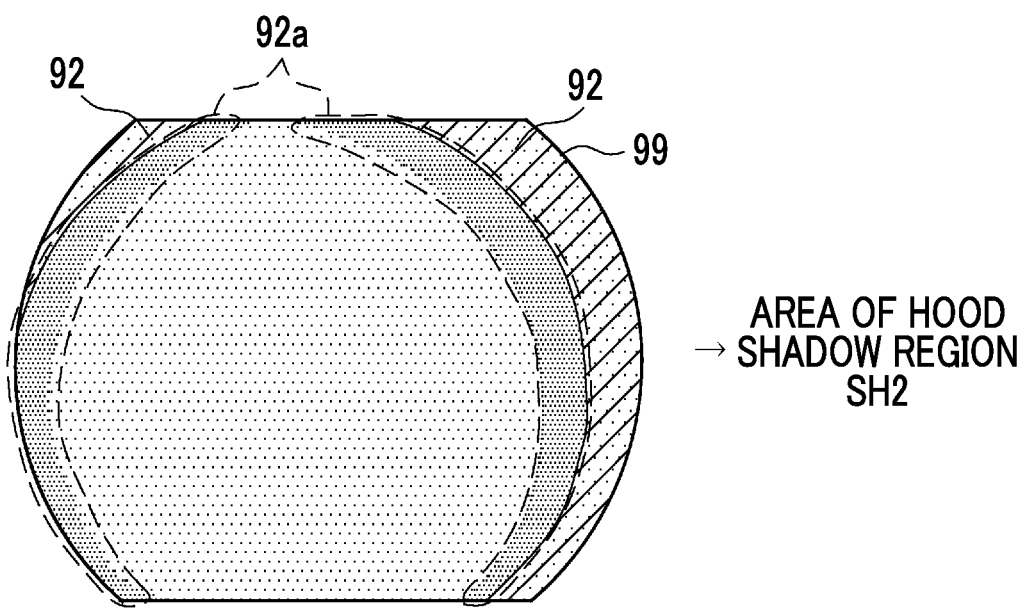

As shown in FIGS. 12A and 12B, the special image 91a and a special image 99 each include a hood shadow region 92a due to the hood 92. The shadow distribution analysis unit 86 calculates the area of the hood shadow region 92a for each image on the basis of the special image 91a and the special image 99. The shadow distribution analysis unit 86 can calculate the area of the hood shadow region 92a by calculating a region in which the brightness value is within a predetermined range, as the hood shadow region 92a, for example, by the image analysis.

An area SH1 of the hood shadow region 92a based on the special image 91a and an area SH2 of the hood shadow region 92a based on the special image 99 are each sent to the image processing implementation control unit 81 in order to decide whether or not to perform image processing on each of the special images 91a and 99. The image processing implementation control unit 81 decides not to perform the image processing on the special image in a case where the calculated area of the hood shadow region 92a is more than a preset threshold value, and decides to perform the image processing on the special image in which the area of the hood shadow region 92a is the preset threshold value or less. For example, the image processing implementation control unit 81 decides not to perform the image processing on the special image 91a because the area SH1 of the hood shadow region 92a based on the special image 91a is more than the preset threshold value, and decides to perform the image processing on the special image 99 because the area SH2 of the hood shadow region 92a based on the special image 99 is the preset threshold value or less.

The auxiliary measurement light analysis unit 87 performs image analysis of the special image related to the position of the auxiliary measurement light. The auxiliary measurement light is used to measure the object to be observed, and the object to be observed is irradiated with the auxiliary measurement light, in addition to illumination light. The auxiliary measurement light is light of color that can be detected by the pixels of the image pickup sensor 44, for example, visible light such as red light having a wavelength range of 600 nm or more and 650 nm or less, and a laser light source or a light emitting element, such as an LED, is used as the auxiliary measurement light.

Figure 13:
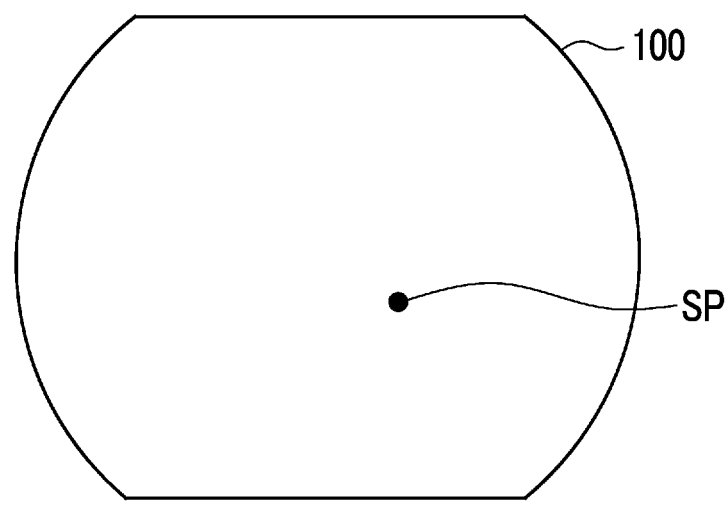
FIG. 13 is an image view of a special image 100 including a spot SP.

As shown in FIG. 13, the object to be observed is irradiated with the auxiliary measurement light, whereby an auxiliary measurement light irradiation region such as a spot SP is formed on the object to be observed. The image of object to be observed on which the spot SP is formed by the auxiliary measurement light is picked up, thereby obtaining a special image 100 including the spot SP which is the auxiliary measurement light irradiation region. The position of the spot SP in the special image 100 is specified, so that the distance between the distal end portion 12d of the endoscope and the object to be observed (hereinafter, referred to as an observation distance) can be obtained.

Figure 14:
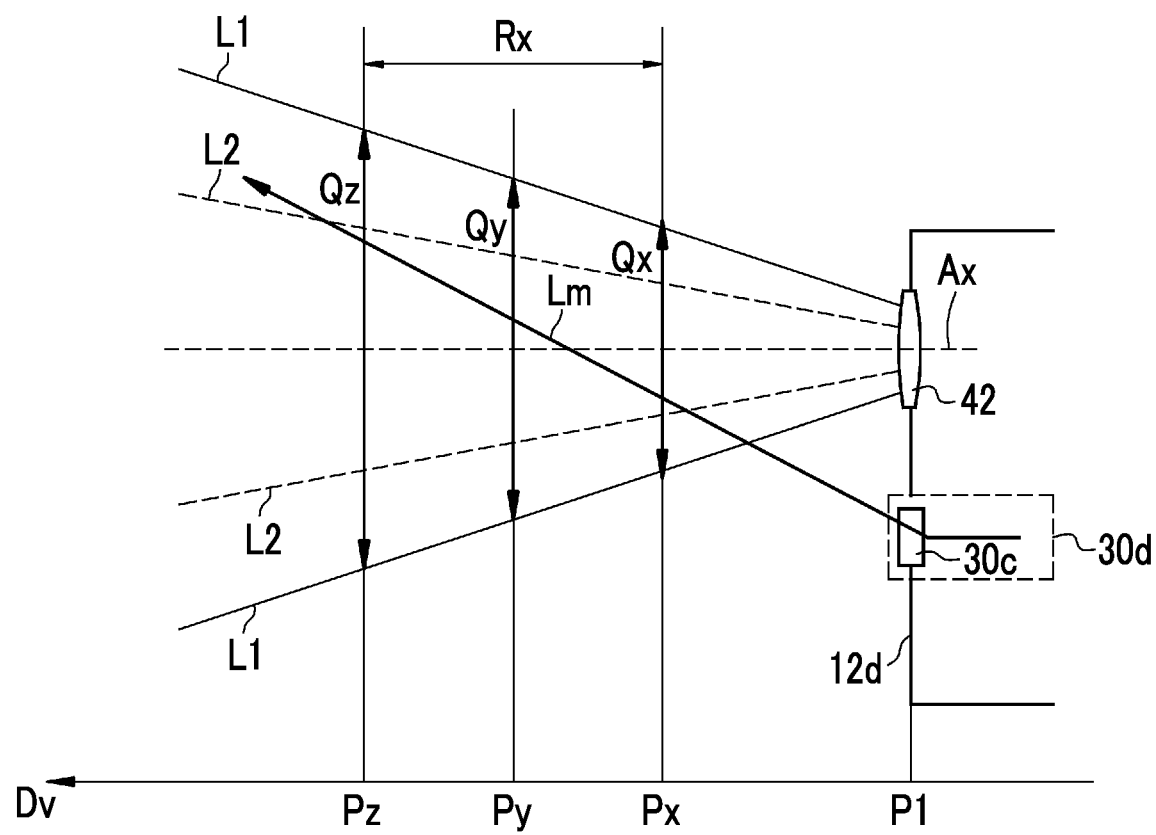
FIG. 14 is a view illustrating the relationship between the position of the spot SP and an observation distance.

The method of obtaining the distance between the distal end portion 12d of the endoscope and the object to be observed from the position of the spot SP in the special image 91a will be described. As shown in FIG. 14, the distal end portion 12d of the endoscope is provided with a lens for auxiliary measurement light 30c, and the object to be observed is irradiated with the auxiliary measurement light emitted from an auxiliary measurement light emitting unit 30d. The auxiliary measurement light is emitted in a state in which an optical axis Lm of the auxiliary measurement light enters the imaging angle of view (within the region sandwiched by the two solid lines L1) of the image pickup optical system. In a case where the object to be observed can be observed in a range Rx of the observation distance, it is understood that the positions (points where the respective arrows Qx, Qy, and Qz cross the optical axis Lm) of the spot SP, which is formed on the object to be observed by the auxiliary measurement light, in image pickup ranges (shown by arrows Qx, Qy, and Qz) at a near end Px, a near middle Py, and a far end Pz of the range Rx are different from each other. The position of the distal end portion 12d of the endoscope is denoted by a position P1. The observation distance is the distance between the distal end portion 12d of the endoscope and the object to be observed. Therefore, the observation distance is the distance between the position P1 and the near end Px, the distance between the position P1 and the near middle Py, and the distance between the position P1 and the far end Pz. The observation distance is, in detail, the distance from the start point of an optical axis Ax of the image pickup optical system 30b at the distal end portion 12d of the endoscope to the object to be observed. An axis Dv indicates the observation distance.

The image of the object to be observed illuminated with the auxiliary measurement light is picked up by the image pickup sensor 44, thereby obtaining a special image including the spot SP which is the auxiliary measurement light irradiation region. In the special image, the position of the spot SP differs depending on the relationship between the optical axis Ax of the image pickup optical system 30b and the optical axis Lm of the auxiliary measurement light, and the observation distance. Accordingly, correspondence information in which the position of the spot SP and the observation distance are associated with each other is acquired in advance, so that the observation distance corresponding to the position of the spot SP can be obtained. Correspondence information in which the observation distance and, for example, a marker with a predetermined size are associated with each other is also acquired in advance in a case where the length or size of the object to be observed is measured. Accordingly, for example, a marker indicating the actual size is superimposed on the special image, so that the actual size of the object to be observed can be measured.

The auxiliary measurement light analysis unit 87 specifies the position of the spot SP in the special image by analyzing the special image including the spot SP. For example, in a case where the distance between the distal end portion 12d of the endoscope and the object to be observed is long, the position of the spot SP is located at the upper part of the special image. Further, for example, in a case where the distance between the distal end portion 12d of the endoscope and the object to be observed is short, the position of the spot SP is located at the central part of the special image. Accordingly, the analysis for specifying the position of the spot SP is performed for the special image, so that it is possible to obtain an index of the distance between the distal end portion 12d of the endoscope and the object to be observed or the resolution of the special image.

Figure 15A:
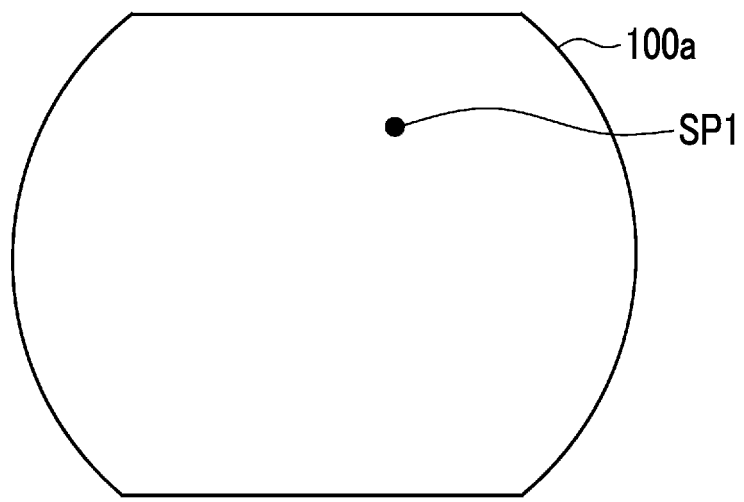
Figure 15B:
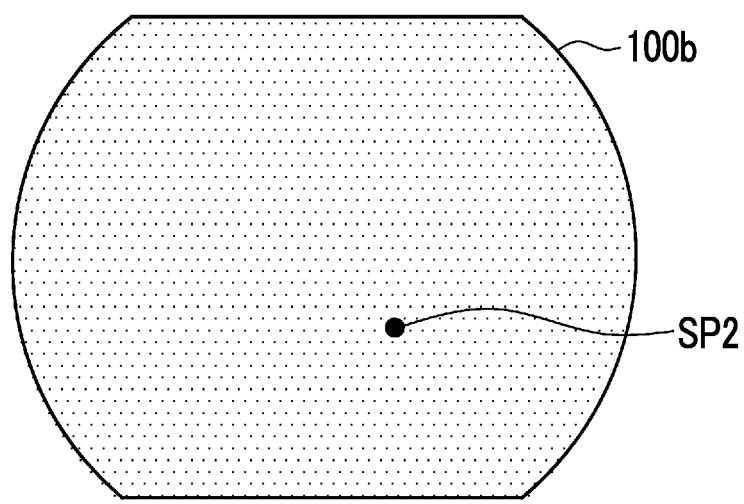

As shown in FIG. 15A, a special image 100a includes a spot SP1 formed on the object to be observed by the auxiliary measurement light. Further, as shown in FIG. 15B, a special image 100b includes a spot SP2 formed on the object to be observed by the auxiliary measurement light. The auxiliary measurement light analysis unit 87 specifies the position of each of the spot SP1 in the special image 100a and the spot SP2 in the special image 100b, for each of the special images 100a and 100b. The auxiliary measurement light analysis unit 87 calculates the observation distance in the special image 100a from the position of the spot SP1 and the observation distance in the special image 100b from the position of the spot SP2 on the basis of the correspondence information in which the position of the spot SP and the observation distance are associated with each other, the correspondence information being acquired in advance by the auxiliary measurement light analysis unit 87. In the present embodiment, it is calculated from the position of the spot SP1 that the observation distance of the special image 100*a* is longer, and it is calculated from the position of the spot SP2 that the observation distance of the special image 100*b* is shorter.

The calculated observation distance is sent to the image processing implementation control unit 81 in order to decide whether or not to perform image processing on the special images 91*a* and 95*a*. The image processing implementation control unit 81 decides to perform the image processing on the special image in a case where the calculated observation distance is a preset threshold value or less, and decides not to perform the image processing on the special image in a case where the observation distance is more than the preset threshold value.

Figure 16:
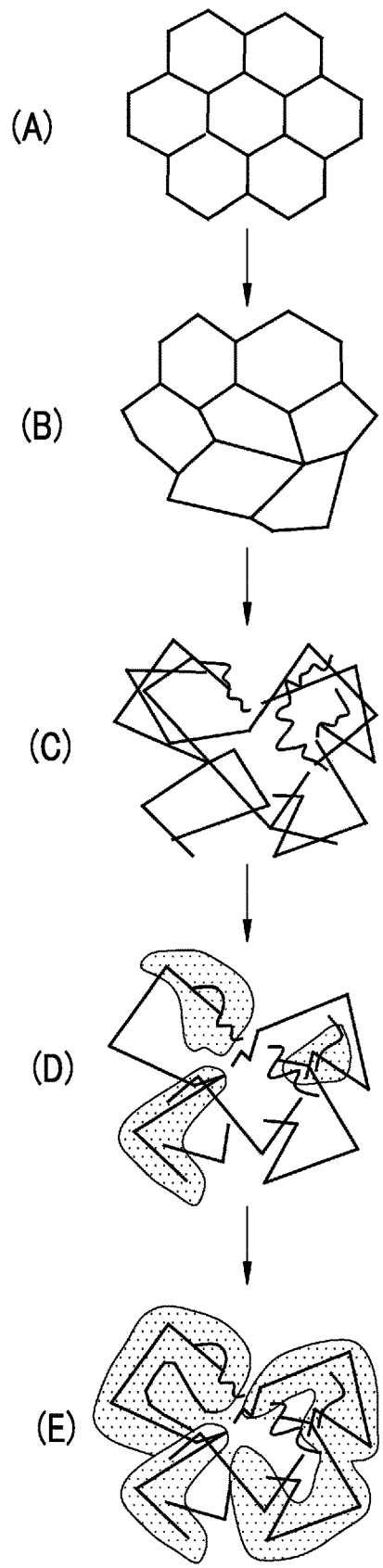
FIG. 16 is a view illustrating the pattern of a vascular structure that varies depending on the severity of ulcerative colitis.

The disease-related processing unit 66 performs, for the special image on which the image processing implementation control unit 81 has decided to perform the image processing, at least one of the calculation of an index value related to the stage of ulcerative colitis, the determination of the stage of ulcerative colitis, or the determination of the remission or non-remission of ulcerative colitis on the basis of the denseness of superficial blood vessels, intramucosal hemorrhage, and extramucosal hemorrhage obtained from the special image. The inventors have found out that ulcerative colitis to be determined by the disease-related processing unit 66 changes the pattern of the vascular structure as the severity worsens, as shown in (A) to (E) of FIG. 16. In a case where ulcerative colitis has remitted or ulcerative colitis has not occurred, the pattern of superficial blood vessels is regular ((A) of FIG. 16) or the regularity of the pattern of the superficial blood vessels is slightly disturbed ((B) of FIG. 16). On the other hand, in a case where ulcerative colitis has not remitted and the severity of ulcerative colitis is mild, the superficial blood vessels are dense ((C) of FIG. 16). Alternatively, in a case where ulcerative colitis has not remitted and the severity of ulcerative colitis is moderate, intramucosal hemorrhage occurs ((D) of FIG. 16). Alternatively, in a case where ulcerative colitis has not remitted and the severity of ulcerative colitis is moderate to severe, extramucosal hemorrhage occurs ((E) of FIG. 16). The disease-related processing unit 66 uses a change in the pattern of the vascular structure to determine the remission or non-remission of ulcerative colitis on the basis of the special image that is one of medical images.

Figure 17:
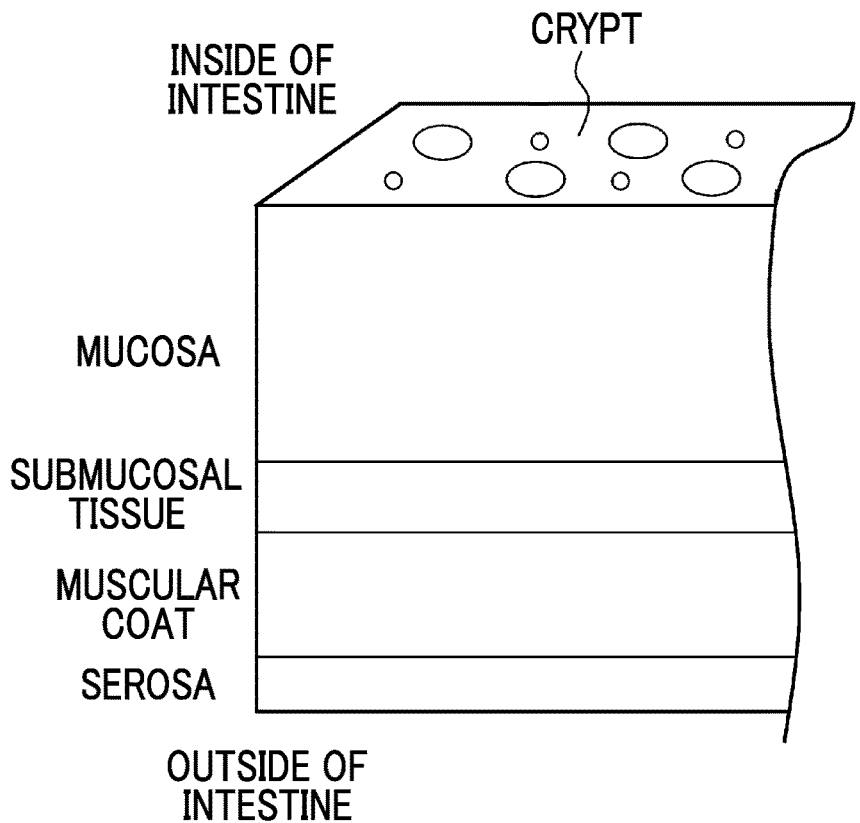
FIG. 17 is a cross-sectional view showing a cross-section of the large intestine.

Here, the "denseness of superficial blood vessels" refers to a state in which superficial blood vessels meander and gather, and refers to a state in which many superficial blood vessels surround the crypt (see FIG. 17) in terms of appearance on the image. The "intramucosal hemorrhage" refers to hemorrhage within the mucosal tissue (see FIG. 17) and requires to be discriminated from hemorrhage into the inner cavity. The "intramucosal hemorrhage" refers to hemorrhage that is not in the mucosa and the inner cavity (the lumen and a hole having plicae) in terms of appearance on the image. The "extramucosal hemorrhage" refers to a small amount of blood that flows into the lumen, blood that oozes out of the lumen or the mucosa positioned in front of the endoscope even after the inside of the lumen has been washed and that can be visually recognized, or intraluminal blood with bleeding on a hemorrhagic mucosa.

Figure 18:
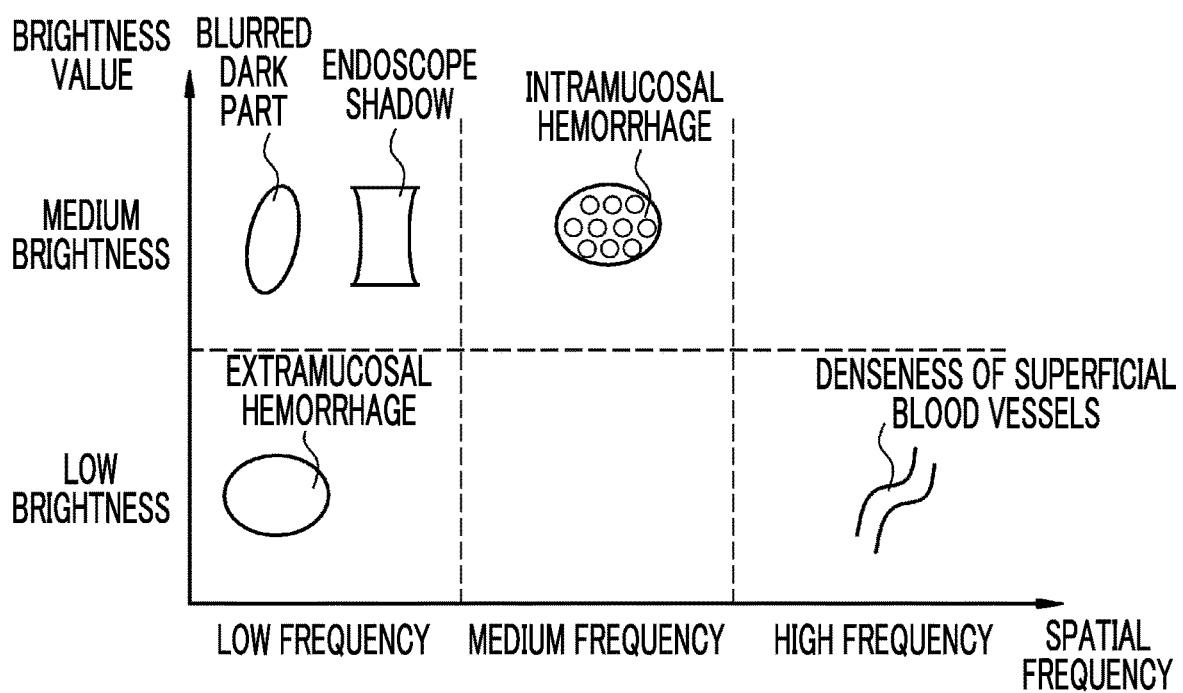
FIG. 18 is a diagram showing the denseness of superficial blood vessels, intramucosal hemorrhage, and extramucosal hemorrhage that are classified depending on a brightness value and a spatial frequency.

The disease-related processing unit 66 classifies the denseness of superficial blood vessels, intramucosal hemorrhage, and extramucosal hemorrhage depending on the frequency characteristic or the brightness value obtained from the special image, and determines the remission or non-remission of ulcerative colitis according to the classification. Specifically, the denseness of superficial blood vessels, intramucosal hemorrhage, and extramucosal hemorrhage are classified as shown in FIG. 18. The denseness of superficial blood vessels is represented by a low brightness value and a high frequency characteristic. The intramucosal hemorrhage is represented by a medium brightness value and a medium frequency characteristic. The extramucosal hemorrhage is represented by a low brightness value and a low frequency characteristic. In a case where various structures of the special image are represented by brightness values and frequency characteristics, a blurred dark part, an endoscope shadow (a shadow that can be generated at the central part of an endoscopic image in a case where the distal end portion 12*d* of the endoscope is moved along the lumen) of the special image, or the like is also included in addition to the above-described three, that is, the denseness of superficial blood vessels, intramucosal hemorrhage, and extramucosal hemorrhage. In the present embodiment, the denseness of superficial blood vessels, intramucosal hemorrhage, and extramucosal hemorrhage that are necessary for the determination of the remission or non-remission of ulcerative colitis are extracted from the special image by using the above-described classification.

As shown in FIG. 6, the disease-related processing unit 66 comprises the spatial frequency component distribution calculation unit 71, the frequency characteristic region extraction unit 72, the structure detection unit 74, and the determination unit 76. The spatial frequency component distribution calculation unit 71 calculates a spatial frequency component distribution by applying Laplacian filter to the special image.

The frequency characteristic region extraction unit 72 extracts a first frequency characteristic region (low frequency region) having a first frequency characteristic (low frequency), extracts a second frequency characteristic region (medium frequency region) having a second frequency characteristic (medium frequency) of which the frequency is higher than the frequency of the first frequency characteristic, and extracts a third frequency characteristic region (high frequency region) having a third frequency characteristic (high frequency) of which the frequency is higher than the frequency of the second frequency characteristic, on the basis of the spatial frequency component distribution.

Figure 19:
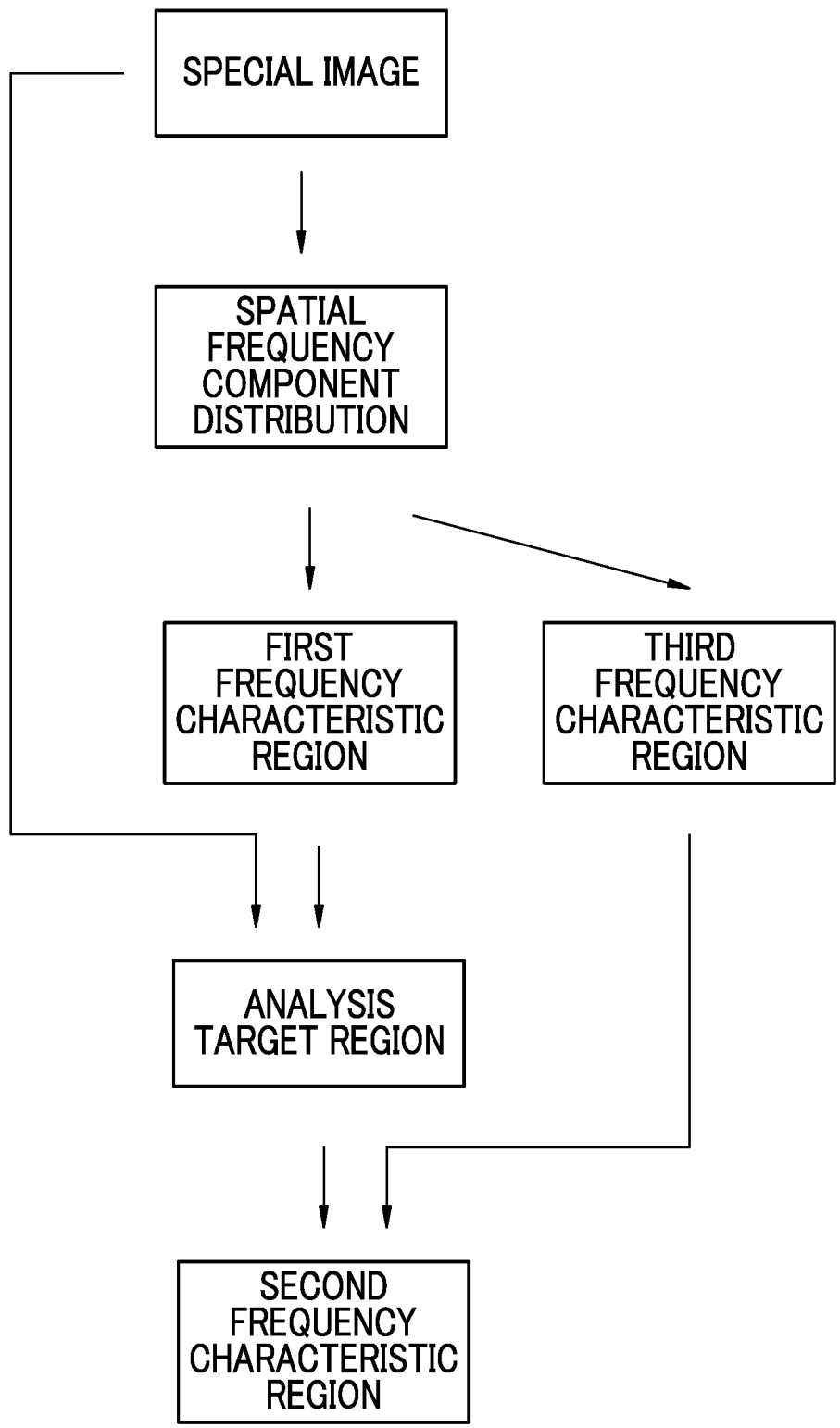
FIG. 19 is a diagram showing a series of flows for extracting a first frequency characteristic region, a second frequency characteristic region, and a third frequency characteristic region.

Specifically, the frequency characteristic region extraction unit 72 comprises a first frequency characteristic region extraction unit 72*a*, a third frequency characteristic region extraction unit 72*b*, an analysis target region detection unit 72*c*, and a second frequency characteristic region extraction unit 72*d*, and extracts the first to third frequency characteristic regions according to the flow shown in FIG. 19. In a case where the standard deviation of the frequencies of nine pixels that are disposed near a part including a specific pixel is a constant value or less, the first frequency characteristic region extraction unit 72*a* determines that the specific pixel is a pixel belonging to the first frequency characteristic on the basis of the spatial frequency component distribution. The first frequency characteristic region extraction unit 72*a* extracts the first frequency characteristic region by detecting the specific pixel for all the pixels. The first frequency characteristic region corresponds to a low frequency region. The third frequency characteristic region extraction unit 72*b* extracts the third frequency characteristic region by Hessian analysis for the spatial frequency component distribution. The third frequency characteristic region corresponds to a high frequency region. In a case where the standard deviation of the frequencies of nine pixels that are disposed near a part including a specific pixel is a constant value or less, the first frequency characteristic region extraction unit 72a determines that the specific pixel is a pixel belonging to the first frequency characteristic. However, in a case where another statistic, for example, the maximum value, the minimum value, or the average value of the frequencies of nine pixels that are disposed near the part is a constant value or less, the first frequency characteristic region extraction unit 72a may determine that the specific pixel is a pixel belonging to the first frequency characteristic.

The analysis target region detection unit 72c detects an analysis target region in which the first frequency characteristic region is excluded from the special image. The second frequency characteristic region extraction unit 72d extracts the second frequency characteristic region by excluding the third frequency characteristic region from the analysis target region. The second frequency characteristic region corresponds to a medium frequency region.

The structure detection unit 74 detects the denseness of superficial blood vessels, intramucosal hemorrhage, and extramucosal hemorrhage on the basis of the first frequency characteristic region that has been subjected to first region discrimination processing using a brightness value, the second frequency characteristic region that has been subjected to second region discrimination processing using a brightness value, and the third frequency characteristic region. Specifically, the structure detection unit 74 detects extramucosal hemorrhage by performing the first region discrimination processing on the first frequency characteristic region, detects intramucosal hemorrhage by performing the second region discrimination processing on the second frequency characteristic region, and detects the third frequency characteristic region as the denseness of superficial blood vessels.

Since the first frequency characteristic region having a low frequency includes a blurred dark part or an endoscope shadow having medium brightness in addition to extramucosal hemorrhage having low brightness, the first region discrimination processing is performed in order to distinguish the blurred dark part, the endoscope shadow, the extramucosal hemorrhage. In the first region discrimination processing, a region of which the brightness value is equal to or less than a threshold value for a brightness value, out of the first frequency characteristic region of the special image, is detected as a region of extramucosal hemorrhage. The second region discrimination processing is performed in order to distinguish intramucosal hemorrhage having medium brightness. In the second region discrimination processing, a region of which the brightness value is equal to or more than a threshold value for a brightness value, out of the second frequency characteristic region of the special image, is detected as a region of intramucosal hemorrhage. Third region discrimination processing may be performed in order to distinguish the denseness of superficial blood vessels having low brightness. In the third region discrimination processing, a region of which the brightness value is equal to or less than a threshold value for a brightness value, out of the third frequency characteristic region of the special image, is detected as a region where superficial blood vessels are dense.

Figure 20:
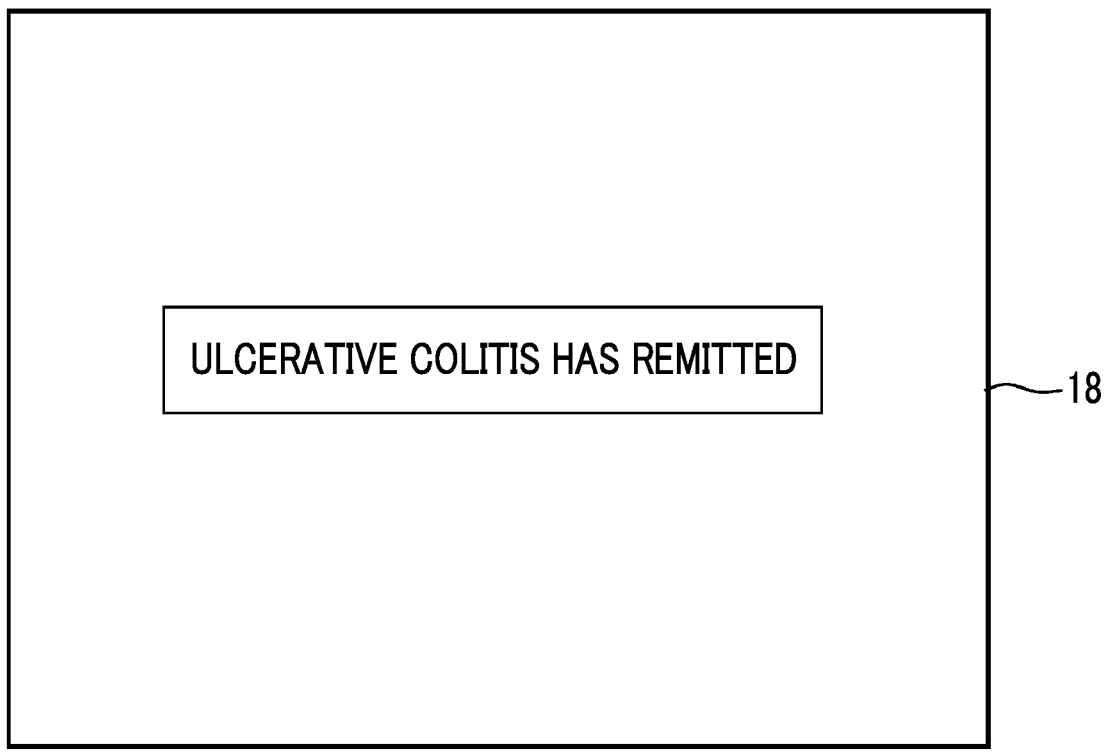
FIG. 20 is an image view of a monitor that displays information regarding determination.

The determination unit 76 determines that ulcerative colitis has not remitted, in a case where any one of a condition in which superficial blood vessels are dense, a condition in which the amount of the detected intramucosal hemorrhage is equal to or more than a threshold value for intramucosal hemorrhage, a condition in which the amount of the detected extramucosal hemorrhage is equal to or more than a threshold value for extramucosal hemorrhage, or a condition in which the sum of the amount of the detected intramucosal hemorrhage and the amount of the detected extramucosal hemorrhage is equal to or more than a threshold value for intramucosal/extramucosal hemorrhage is satisfied. On the other hand, the determination unit 76 determines that ulcerative colitis has remitted, in a case where all of the condition in which superficial blood vessels are dense, the condition in which the amount of the detected intramucosal hemorrhage is equal to or more than the threshold value for intramucosal hemorrhage, the condition in which the amount of the detected extramucosal hemorrhage is equal to or more than the threshold value for extramucosal hemorrhage, and the condition in which the sum of the amount of the detected intramucosal hemorrhage and the amount of the detected extramucosal hemorrhage is equal to or more than the threshold value for intramucosal/extramucosal hemorrhage are not satisfied. Information regarding the above-described determination of the determination unit 76 is displayed on the monitor 18, and is used for the user to determine the remission or non-remission of ulcerative colitis. In a case where the determination unit 76 determines that ulcerative colitis has remitted, a message that ulcerative colitis has remitted is displayed on the monitor 18 as shown in FIG. 20. It is preferable that the special image used for the determination of the determination unit 76 is superimposed and displayed in a case where the information regarding the determination is displayed.

It is preferable that the determination unit 76 calculates the amount of the detected intramucosal hemorrhage on the basis of a ratio of the second frequency characteristic region to the special image. Further, it is preferable that the determination unit 76 calculates the amount of the detected extramucosal hemorrhage on the basis of a ratio of the first frequency characteristic region having low brightness (the first frequency characteristic region that has been subjected to the first region discrimination processing) to the special image. Alternatively, the determination unit 76 may obtain an index value indexing the severity of ulcerative colitis in addition to or instead of the determination of the remission or non-remission of ulcerative colitis, determine the remission or non-remission of ulcerative colitis according to the index value, and make the monitor 18 display the index value as a determination result.

In a case where units in the disease-related processing unit 66 have the same function, for example, as in the frequency characteristic analysis unit 84 and the spatial frequency component distribution calculation unit 71, the units may be made common. That is, one unit may be made to function as the frequency characteristic analysis unit 84 in some cases, and to function as the spatial frequency component distribution calculation unit 71 in another case.

As described above, in a case of determining ulcerative colitis by using a medical image, by the image processing device in which the image processing decision unit 70 decides whether or not to perform image processing on the special image on the basis of the imaging condition of the special image, which is a medical image, and/or the image analysis result obtained by analyzing the special image, the disease-related processing unit 66 performs, for the special image on which the image processing decision unit 70 has decided to perform the image processing, at least one of the calculation of the index value related to the stage of ulcerative colitis, the determination of the stage of ulcerative colitis, or the determination of the remission or non-remission of ulcerative colitis on the basis of the denseness of superficial blood vessels, intramucosal hemorrhage, and extramucosal hemorrhage, the image processing is performed on the special image in which the determination result of the image processing can be accurately obtained. Accordingly, it is possible to accurately determine ulcerative colitis by using the special image.

In some cases, the image processing implementation control unit 81 decides whether or not to perform image processing on the basis of the imaging condition of the special image and/or the image analysis result obtained by analyzing the special image according to the preset contents. Therefore, the image processing is performed on the automatically selected special image. Accordingly, it is possible to accurately and easily determine ulcerative colitis by using the special image.

Figure 21:
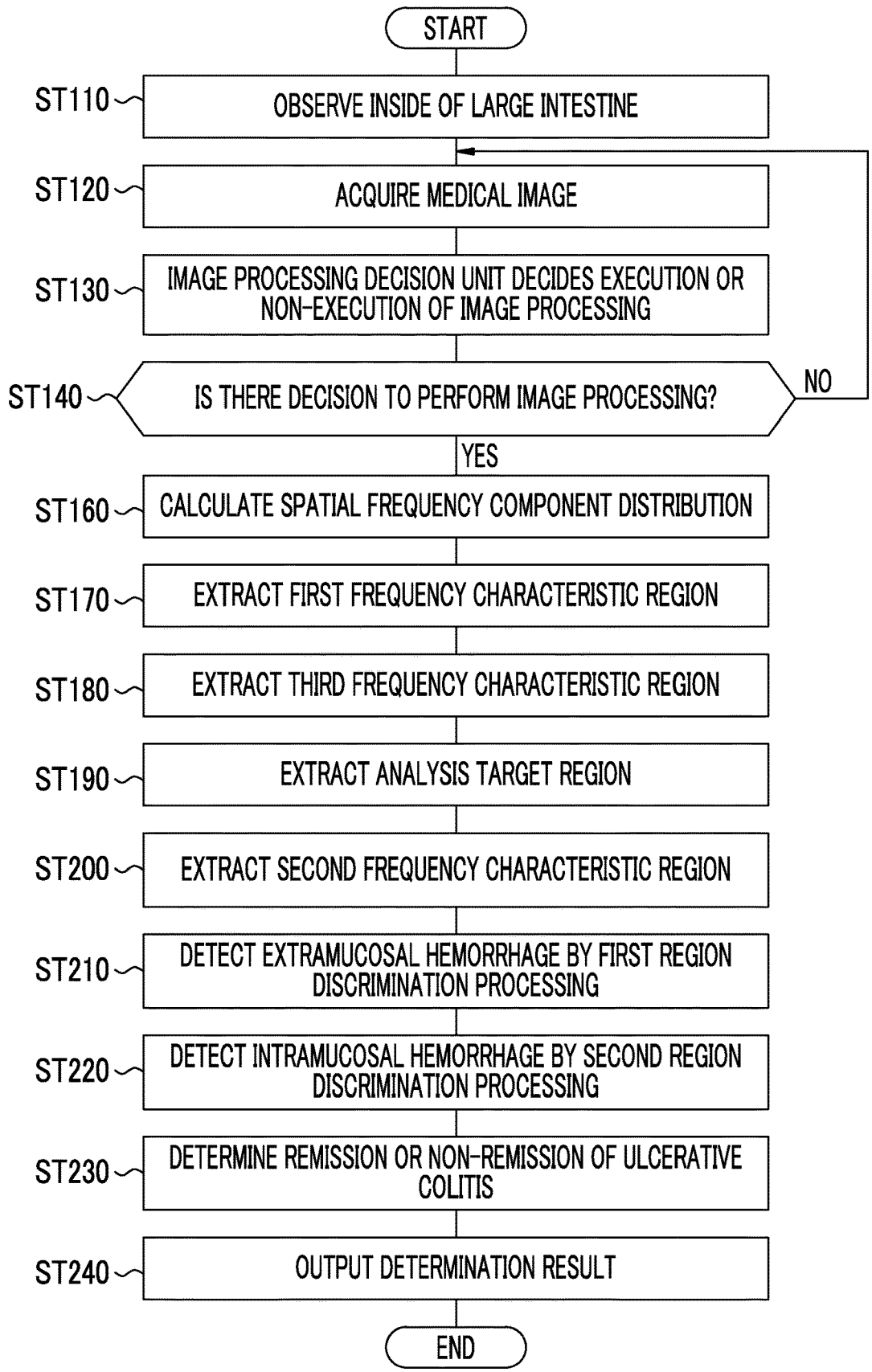
FIG. 21 is a flowchart showing a series of flows of a disease-related processing mode.

Next, a series of flows of the disease-related processing mode will be described with reference to the flowchart shown in FIG. 21. In a case where a mode is switched to the disease-related processing mode, the object to be observed is irradiated with special light. The endoscope 12 picks up the image of the object to be observed illuminated with special light (step ST110), thereby obtaining a special image, which is one of endoscopic images (medical images), at a certain time point. The image acquisition unit 50 acquires the special image from the endoscope 12 (step ST120).

The special image is sent to the disease-related processing unit 66, and the image processing decision unit 70 decides whether or not to perform image processing, that is, the execution or non-execution of image processing (step ST130). In the present embodiment, two kinds of analysis, that is, frequency characteristics and halation distribution, are performed, and the image processing implementation control unit 81 integrates these analysis results to decide the execution or non-execution of image processing.

The frequency characteristic analysis unit 84 calculates the frequency characteristics of the special image and creates a spatial frequency distribution image. The spatial frequency distribution image can be created by applying a filter of each color in response to the spatial frequency. For example, a low frequency region 98*a* is colored blue, a high frequency region 98*b* is colored red or the like. The frequency characteristic analysis unit 84 calculates, for example, an area having a frequency of F or less in the spatial frequency distribution image and compares the calculated area with a preset threshold value for the low frequency region. The comparison is performed by, for example, Expression (1). Here, the area having a frequency of F or less is denoted by Area (Frequency≤F), and the threshold value for the low frequency region is denoted by Threshold_Lowfrequency. A special image that satisfies Expression (1) indicates that the object to be observed is far from the distal end portion 12*d* of the endoscope or that the deep part of the lumen exists.

$$\text{Area(Frequency}\leq F)>\text{Threshold\_Lowfrequenc} \tag{1}$$

Next, the halation distribution analysis unit 83 calculates the halation distribution of the special image and creates a halation distribution image. The halation distribution image can be created by calculating a region where the brightness value is a specific value or more. For example, the halation distribution image can be created by applying a filter of each color to a region where the brightness value is a specific brightness value or more in response to the specific value. For example, the halation region is colored white or the like. The halation distribution analysis unit 83 calculates, for example, an area having a brightness value of S or more in the halation distribution image and compares the calculated area with a preset threshold value for the halation region. The comparison is performed, for example, by Expression (2). Here, the area having a brightness value of S or more is denoted by Area (Signal≥S), and the threshold value for the halation region is denoted by Threshold_Halarion. The special image that satisfies Expression (2) indicates that a halation region indicating that the object to be observed is close to the distal end portion 12*d* of the endoscope does not exist.

$$\text{Area(Signal}\geq S)<\text{Threshold\_Halarion} \tag{2}$$

Figure 22:
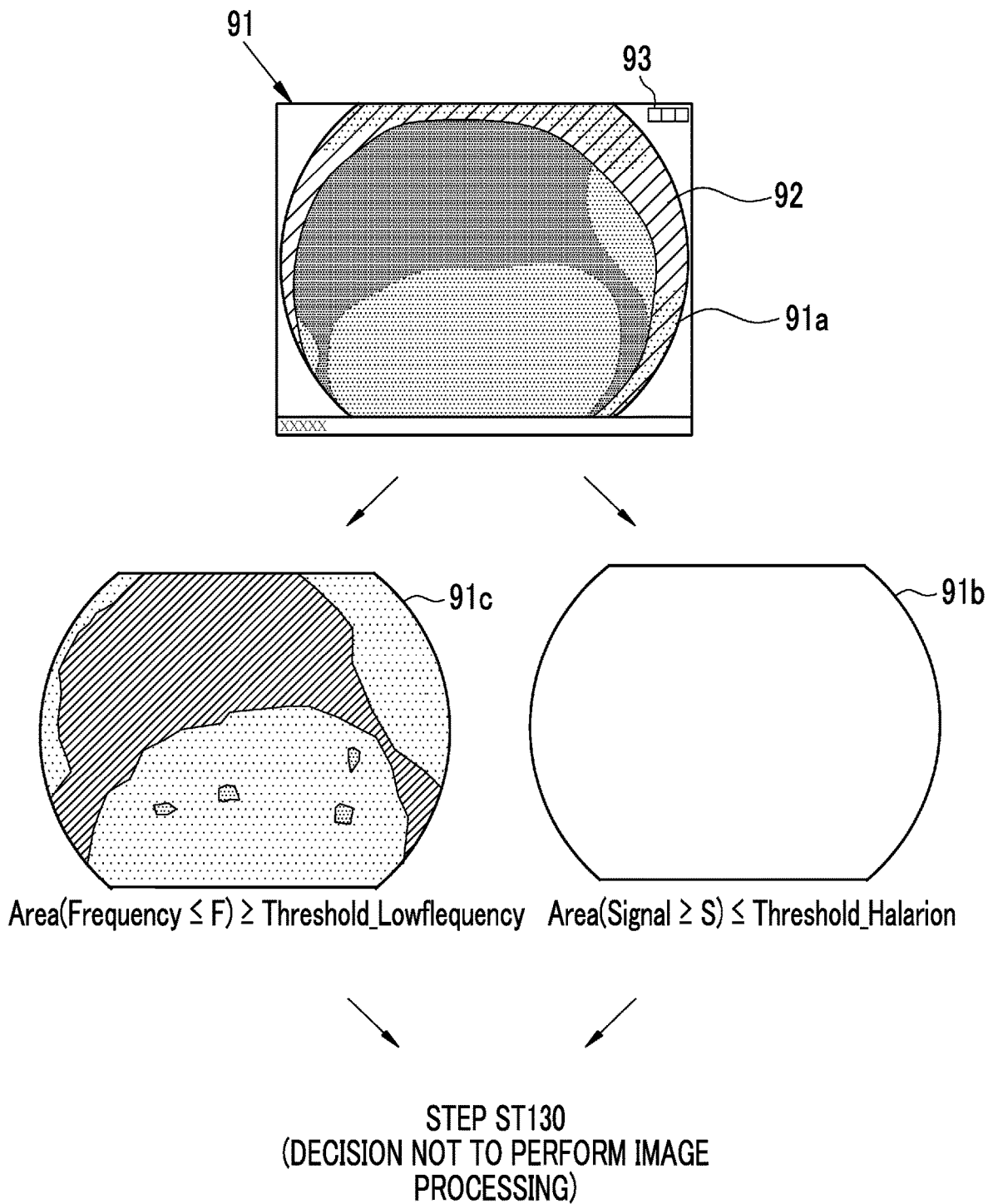
FIG. 22 is a view illustrating a case where decision is made in step ST130 that image processing is not executed.

The image processing implementation control unit 81 receives the area Area (Frequency≤F) of the low frequency region 98*a* from the frequency characteristic analysis unit 84 and the area Area (Signal≥S) of the halation region from the halation distribution analysis unit 83, and compares the received areas with the respective threshold values by Expressions (1) and (2). Further, the special image that satisfies Expressions (1) and (2) is not suitable for image processing, for example, to determine the stage of ulcerative colitis because the special image is an image in which the distance from the distal end portion 12*d* of the endoscope to the object to be observed is long and the resolution is low. Therefore, image processing decision unit 70 decides not to implement image processing (No in step ST140). For example, as shown in FIG. 22, the spatial frequency distribution image 91*c* based on the special image 91*a* satisfies Expression (1), and the halation distribution image 91*b* based on the special image 91*a* satisfies Expression (2). Therefore, the image processing decision unit 70 decides not to perform image processing. The image acquisition unit 50 acquires a medical image again in a case where the image processing decision unit 70 decides not to perform the image processing.

Figure 23:
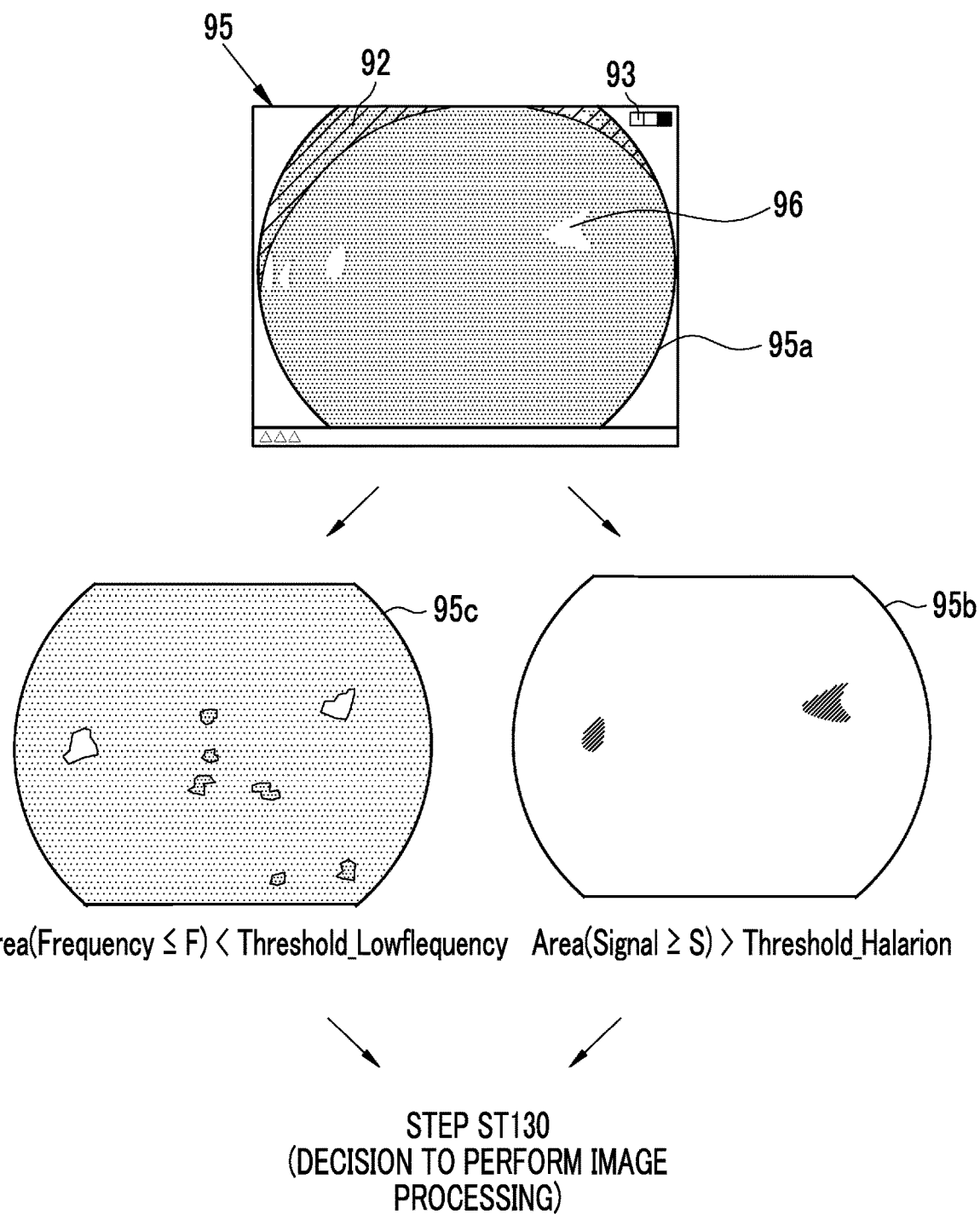
FIG. 23 is a view illustrating a case where decision is made in step ST130 that image processing is executed.

Alternatively, the special image that does not satisfy Expressions (1) and (2) is suitable for image processing, for example, to determine the stage of ulcerative colitis because the special image is an image in which the distance from the distal end portion 12*d* of the endoscope to the object to be observed is short and the resolution is high. Therefore, image processing decision unit 70 decides to implement image processing (Yes in step ST140). For example, as shown in FIG. 23, in the special image 95*a*, the spatial frequency distribution image 95*c* based on the special image 95*a* does not satisfy Expression (1), and the halation distribution image 95*b* based on the special image 95*a* does not satisfy Expression (2). Therefore, the image processing decision unit 70 decides to perform image processing. In a case where the image processing decision unit 70 decides to perform the image processing, the process proceeds to the next step.

Alternatively, the special image that satisfies any one of Expression (1) or Expression (2) cannot be said to be suitable for image processing, for example, to determine the stage of ulcerative colitis, but has no problem because the special image is an image in which the distance from the distal end portion 12*d* of the endoscope to the object to be observed is short and the resolution is high. Therefore, image processing decision unit 70 decides to implement image processing (Yes in step ST140).

The image processing is performed on the special image on which the image processing decision unit 70 has decided to implement the image processing. The spatial frequency component distribution calculation unit 71 calculates a spatial frequency component distribution from the special image (step ST160). The first frequency characteristic region extraction unit 72*a* extracts a first frequency characteristic region having a low frequency on the basis of the spatial frequency component distribution (step ST170). Further, the third frequency characteristic region extraction unit 72*b* extracts a third frequency characteristic region having a high frequency on the basis of the spatial frequency component distribution (step ST180). The analysis target region detection unit 72*c* detects an analysis target region in which the first frequency characteristic region is excluded from the medical image (step ST190). The second frequency characteristic region extraction unit 72*d* extracts a second frequency characteristic region having a medium frequency by excluding the third frequency characteristic region from the analysis target region (step ST200).

The structure detection unit 74 performs the first region discrimination processing on the first frequency characteristic region having a low frequency to detect extramucosal hemorrhage (step ST210). Further, the structure detection unit 74 performs the second region discrimination processing on the second frequency characteristic region having a medium frequency to detect intramucosal hemorrhage (step ST220). Further, the structure detection unit 74 detects the third frequency characteristic region as the denseness of superficial blood vessels.

The determination unit 76 determines the remission or non-remission of ulcerative colitis on the basis of the denseness of superficial blood vessels, intramucosal hemorrhage, and extramucosal hemorrhage that are detected by the structure detection unit 74 (step ST230). Information regarding the determination of the determination unit 76 is displayed on the monitor 18 (step ST240).

Figure 24:
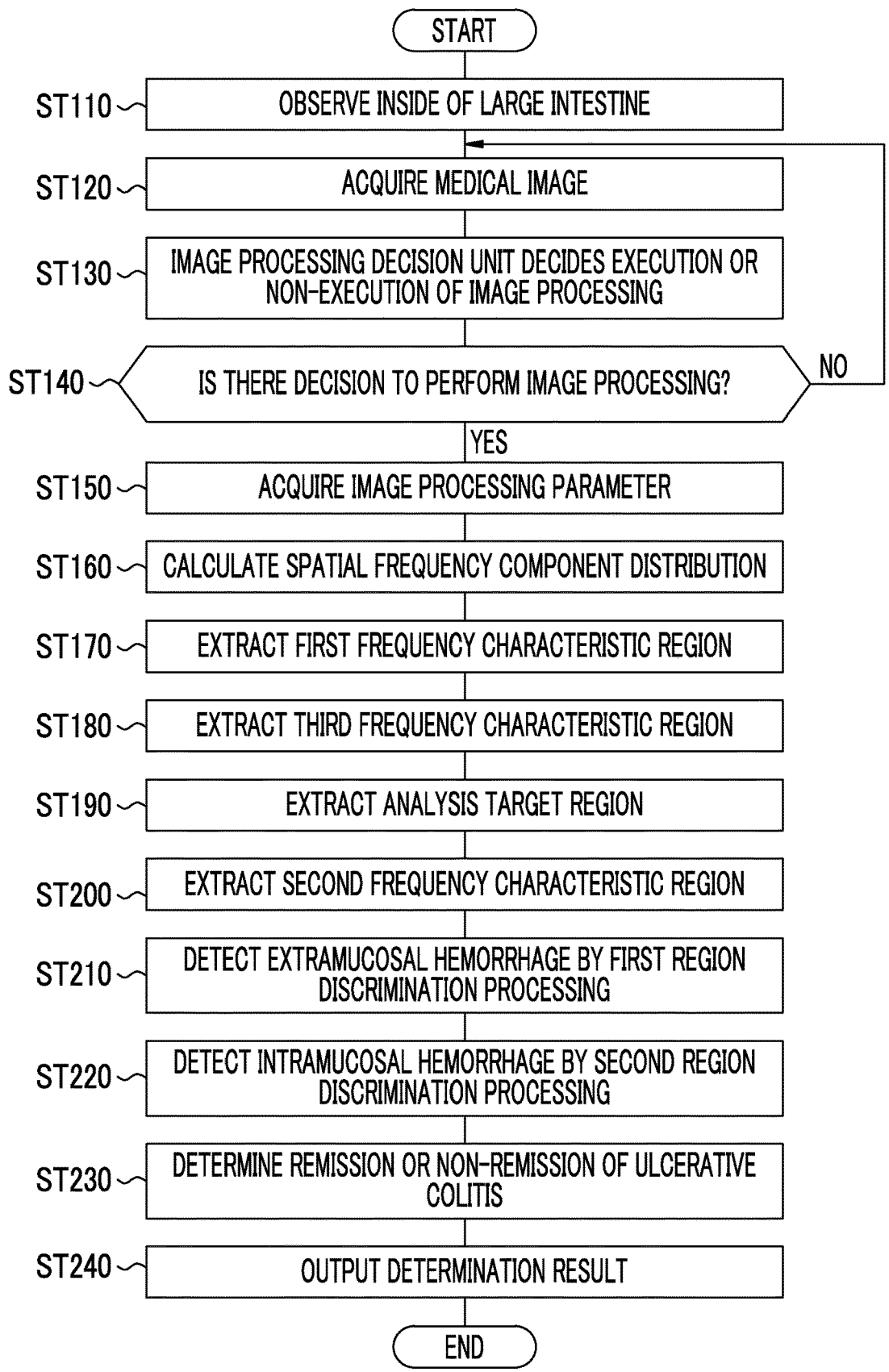
FIG. 24 is a flowchart showing a series of flows of a disease-related processing mode including step ST150.

A series of flows of the disease-related processing mode using the imaging condition of the special image and/or the image analysis result obtained by analyzing the special image, which is sent from the image processing implementation control unit 81, performed by the disease-related processing unit 66 for the special image on which the image processing decision unit 70 has decided to perform the image processing will be described with reference to the flowchart shown in FIG. 24. The flowchart shown in FIG. 24 is a flowchart in which step ST150 is added to the flowchart shown in FIG. 21. That is, image processing parameters that are the imaging condition of the special image and/or the image analysis result obtained by analyzing the special image are acquired from the image processing implementation control unit 81 (step ST150) before the image processing is performed for the special image on which the image processing decision unit 70 has decided to implement the image processing.

With regard to the image processing parameter, for example, on the basis of the finding that the severity of inflammatory diseases is more severe as the region where blood vessels are dense is more, in a case where the magnification ratio of the object to be observed included in the special image is small, it is also necessary to reduce the kernel size used to calculate the density of superficial blood vessels when the density of superficial blood vessels is calculated in order to evaluate the denseness of superficial blood vessels. Determination can be made that the magnification ratio of the special image which satisfies both Expressions (1) and (2) is small Therefore, the image processing implementation control unit 81 sends an image processing result that the special image satisfies both Expressions (1) and (2) to the disease-related processing unit 66. The disease-related processing unit 66 sets an image processing parameter that a kernel for a low magnification ratio is used, from among several types of kernel sizes prepared in advance, as a kernel size in a case where the density of superficial blood vessels is calculated by using the image processing result that the special image satisfies both Expressions (1) and (2), which is sent from the image processing implementation control unit 81. The subsequent flows are the same as the flows of the flowchart shown in FIG. 21.

Second Embodiment

In a second embodiment, the object to be observed is illuminated by using a broadband light source, such as a xenon lamp, and a rotary filter instead of the four-color LEDs 20*a* to 20*d* shown in the first embodiment. Further, the image of the object to be observed is picked up by a monochrome image pickup sensor in place of the color image pickup sensor 44. Other than that, the configurations are the same as those of the first embodiment.

Figure 25:
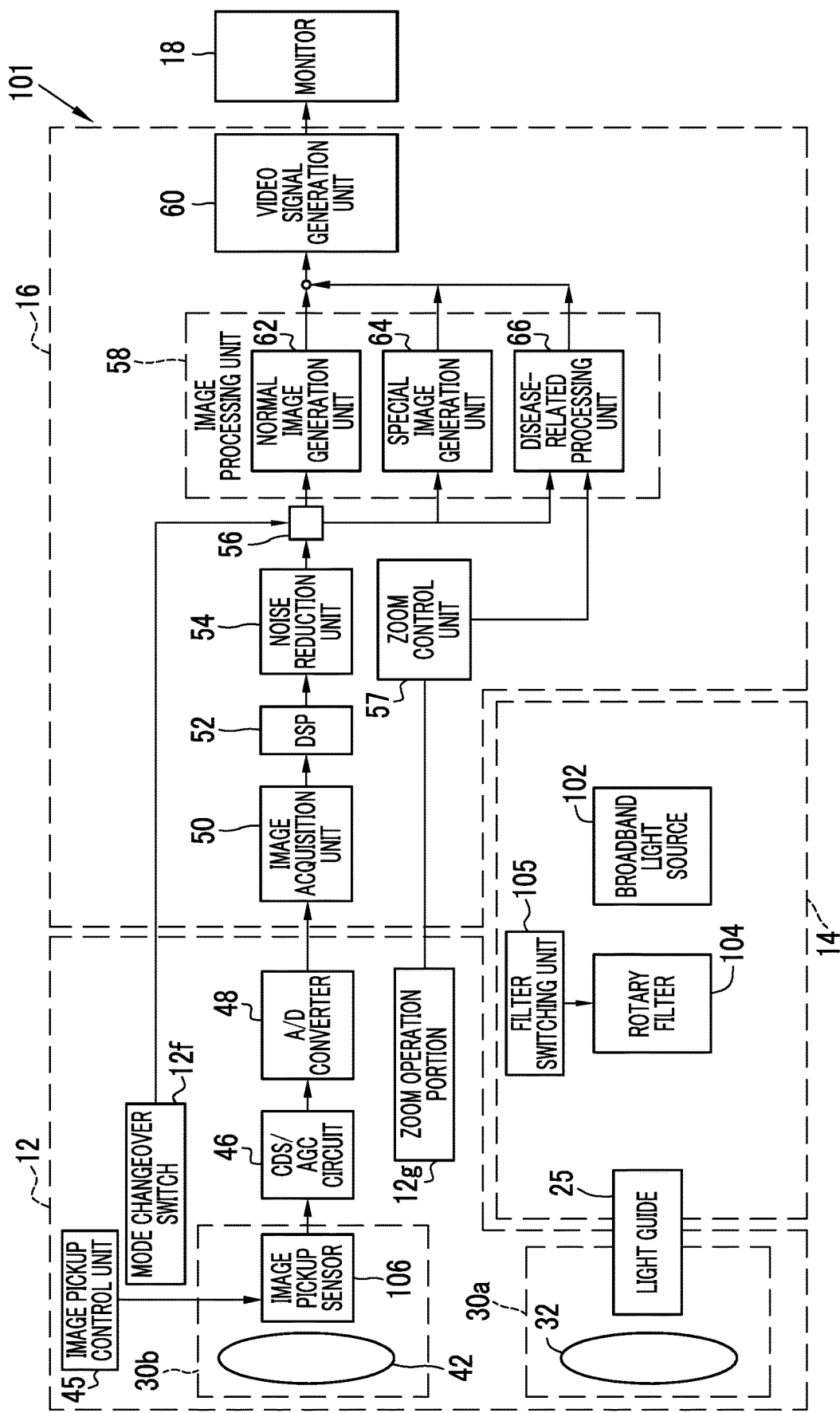
FIG. 25 is a block diagram showing the functions of an endoscope system of a second embodiment.

As shown in FIG. 25, in an endoscope system 100 of the second embodiment, the light source device 14 is provided with a broadband light source 102, a rotary filter 104, and a filter switching unit 105, in place of the four-color LEDs 20*a* to 20*d*. Further, the image pickup optical system 30*b* is provided with a monochrome image pickup sensor 106 in which a color filter is not provided, instead of the color image pickup sensor 44.

The broadband light source 102 is a xenon lamp, a white LED, or the like, and emits white light having a wavelength range ranging from blue light to red light. The rotary filter 104 is provided with a filter 107 for a normal light mode and a filter 108 for a special light mode and a disease-related processing mode that are disposed in order from the inside (see FIG. 26). The filter switching unit 105 moves the rotary filter 104 in a radial direction, and inserts the filter 107 for a normal light mode into the optical path of white light in a case where the normal light mode is set by the mode changeover SW 12*f* and inserts the filter 108 for a special light mode and a disease-related processing mode into the optical path of white light in a case where the special light mode or the disease-related processing mode is set.

Figure 26:
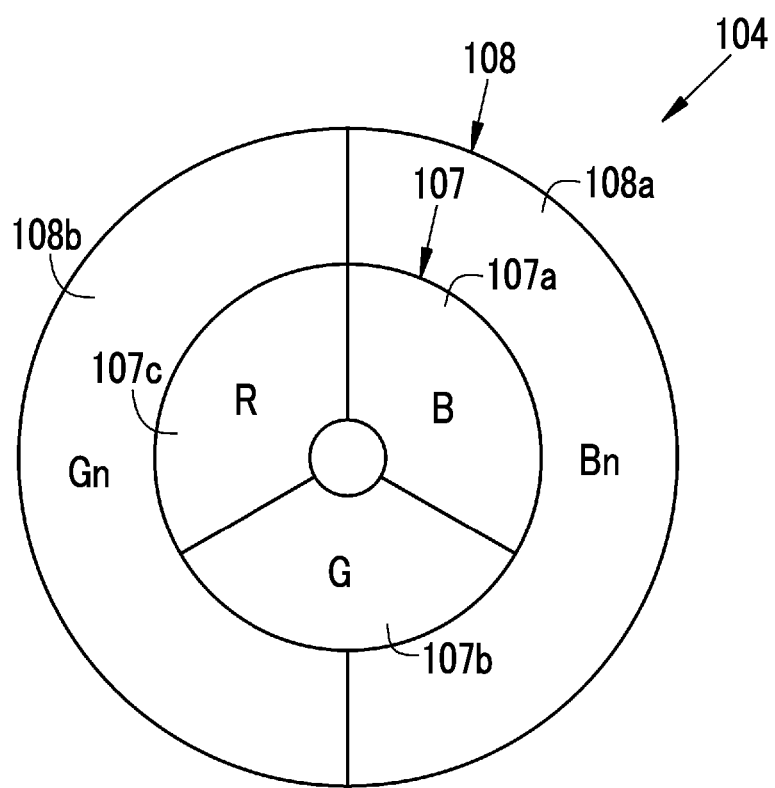
FIG. 26 is a plan view of a rotary filter.

As shown in FIG. 26, the filter 107 for a normal light mode is provided with a B filter 107*a*, a G filter 107*b*, and an R filter 107*c* that are disposed along a circumferential direction. The B filter 107*a* transmits broadband blue light B of white light, the G filter 107*b* transmits broadband green light G of white light, and the R filter 107*c* transmits broadband red light R of white light. Therefore, in the normal light mode, the rotary filter 104 is rotated to allow the object to be observed to be alternately irradiated with broadband blue light B, broadband green light G, and broadband red light R, as normal light.

The filter 108 for a special light mode and a disease-related processing mode is provided with a Bn filter 108*a* and a Gn filter 108*b* that are disposed along the circumferential direction. The Bn filter 108*a* transmits narrow-band blue light of white light, and the Gn filter 108*b* transmits narrow-band green light of white light. Therefore, in the special light mode or the disease-related processing mode, the rotary filter 104 is rotated to allow the object to be observed to be alternately irradiated with narrow-band blue light and narrow-band green light as short-wavelength light, as special light. The wavelength range of the narrow-band blue light is preferably 400 to 450 nm and the wavelength range of the narrow-band green light is preferably 540 to 560 nm.

In the endoscope system 100, the image of the object to be observed is picked up by the monochrome image pickup sensor 106 each time the object to be observed is illuminated with broadband blue light B, broadband green light G, and broadband red light R in the normal light mode. With this, Bc image signals, Gc image signals, and Rc image signals can be obtained. Then, a normal image is generated on the basis of these three-color image signals by the same method as that of the first embodiment.

In the endoscope system 100, the image of the object to be observed is picked up by the monochrome image pickup sensor 106 each time the object to be observed is illuminated with narrow-band blue light and narrow-band green light in the special light mode or the disease-related processing mode. With this, Bs image signals and Gs image signals can be obtained. Then, a special image is generated on the basis of these two-color image signals by the same method as that of the first embodiment.

Third Embodiment

In a third embodiment, the object to be observed is illuminated by using a laser light source and a phosphor instead of the four-color LEDs 20a to 20d shown in the first embodiment. In the following, only parts different from those of the first embodiment will be described and the description of substantially the same parts as those of the first embodiment will not be repeated.

Figure 27:
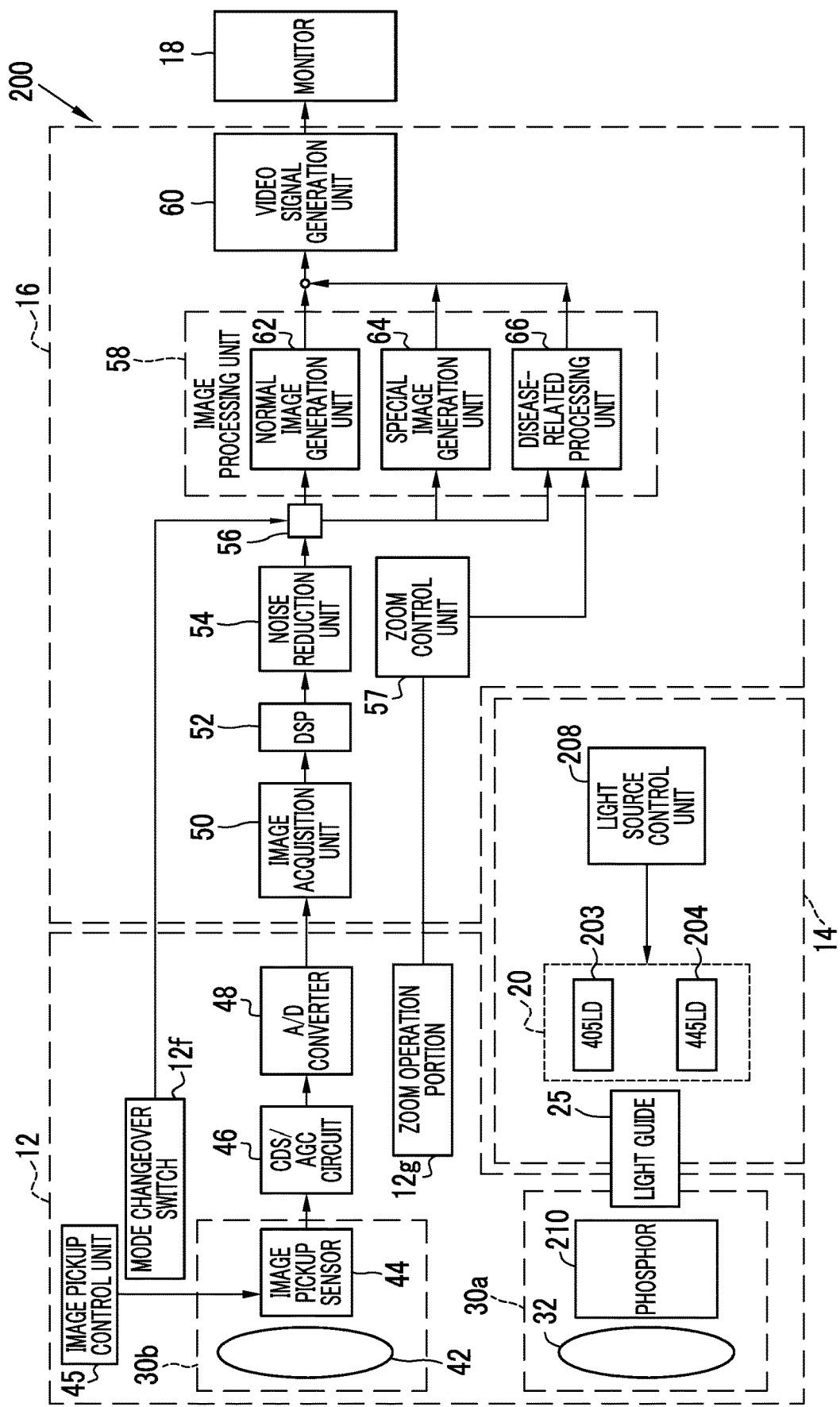
FIG. 27 is a block diagram showing the functions of an endoscope system of a third embodiment.

As shown in FIG. 27, in an endoscope system 200 of the third embodiment, the light source unit 20 of the light source device 14 is provided with a violet laser light source unit 203 (denoted by "405LD", LD represents a laser diode) that emits violet laser light having a central wavelength of 405±10 nm corresponding to short-wavelength light and a blue laser light source unit (denoted by "445LD") 204 that emits blue laser light having a central wavelength of 445±10 nm, in place of the four-color LEDs 20a to 20d. The emission of light from semiconductor light emitting elements of these respective light source units 203 and 204 is individually controlled by a light source control unit 208.

The light source control unit 208 turns on the blue laser light source unit 204 in a case of the normal light mode. Meanwhile, the light source control unit 208 simultaneously turns on the violet laser light source unit 203 and the blue laser light source unit 204 in a case of the special light mode or the disease-related processing mode.

It is preferable that the half-width of violet laser light, blue laser light, or blue-green laser light is set to about ±10 nm. Further, broad area-type InGaN-based laser diodes can be used as the violet laser light source unit 203 and the blue laser light source unit 204, and InGaNAs-based laser diodes or GaNAs-based laser diodes can also be used. A configuration using a light emitter such as a light emitting diode may be adopted as the light source.

The illumination optical system 30a is provided with a phosphor 210 on which blue laser light or blue-green laser light from the light guide 25 is incident, in addition to the illumination lens 32. The phosphor 210 is excited by blue laser light and emits fluorescence. Therefore, blue laser light corresponds to excitation light. Further, a part of blue laser light is transmitted without exciting the phosphor 210. Blue-green laser light is transmitted without exciting the phosphor 210. The inside of the body of the object to be observed is illuminated with light emitted from the phosphor 210 through the illumination lens 32.

Figure 28:
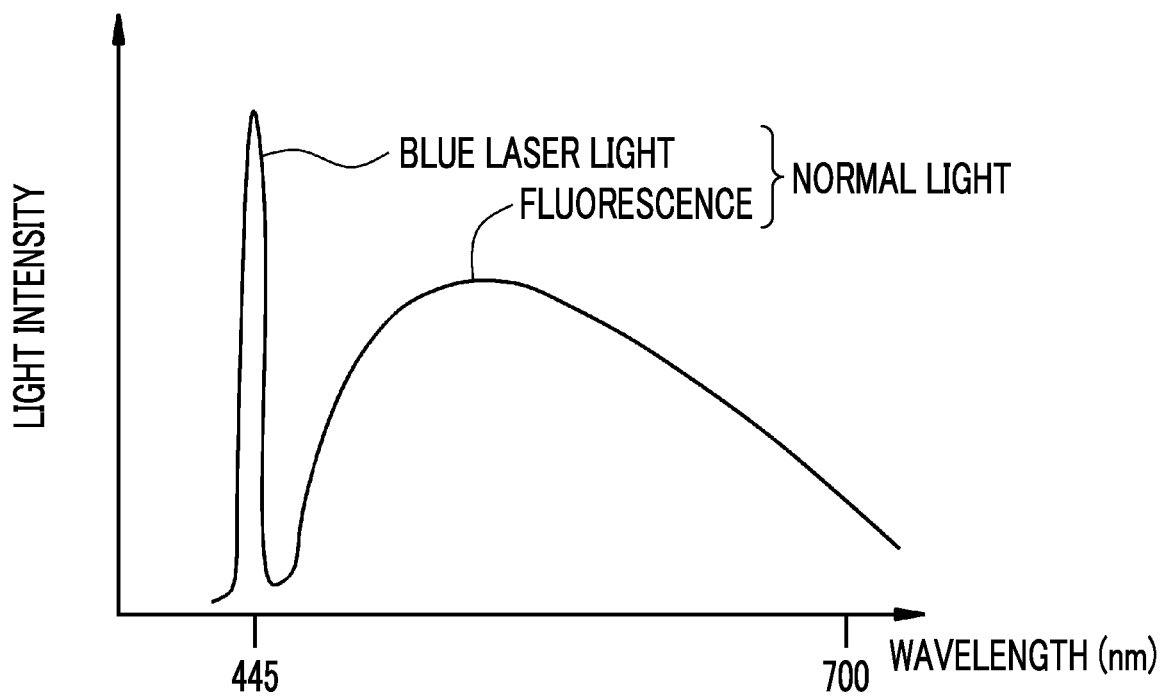
FIG. 28 is a graph showing the spectrum of normal light of the third embodiment.

Here, since blue laser light is mainly incident on the phosphor 210 in the normal light mode, the object to be observed is illuminated with normal light in which blue laser light and fluorescence that is excited and emitted from the phosphor 210 by blue laser light are multiplexed, as shown in FIG. 28. The image of the object to be observed illuminated with the normal light is picked up by an image pickup sensor 44, so that a normal image consisting of Bc image signals, Gc image signals, and Rc image signals can be obtained.

Figure 29:
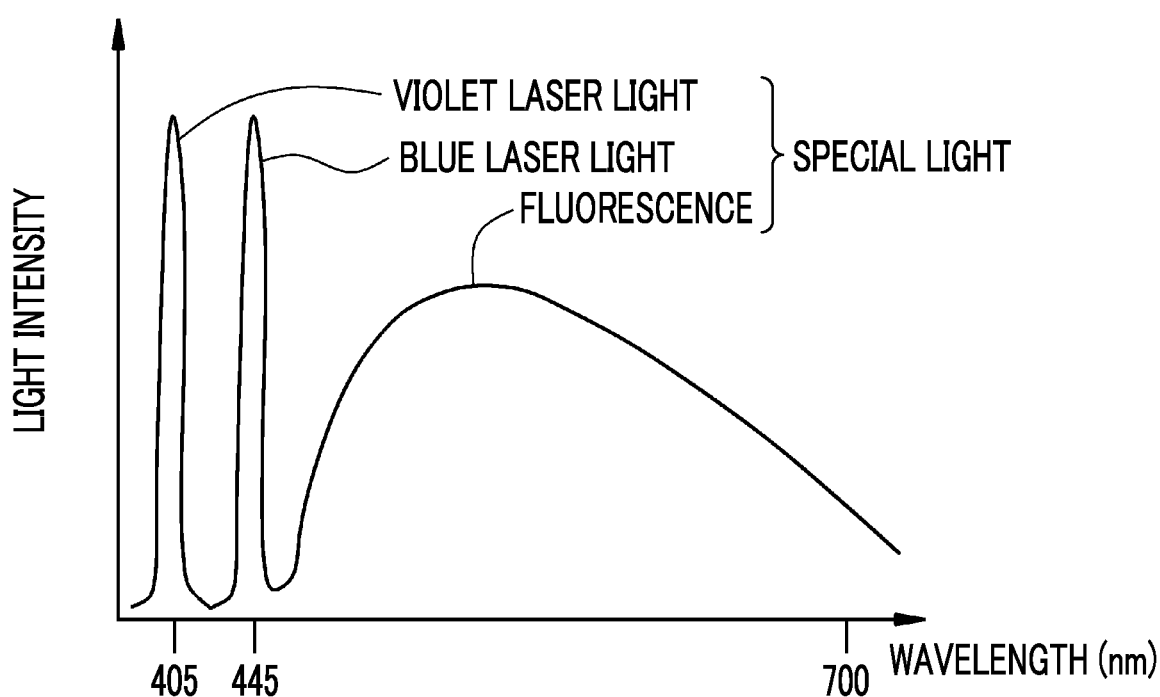
FIG. 29 is a graph showing the spectrum of special light of the third embodiment.

Further, violet laser light and blue laser light are simultaneously incident on the phosphor 210 in the special light mode or the disease-related processing mode, whereby pseudo white light including fluorescence that is excited and emitted from the phosphor 210 by violet laser light and blue laser light is emitted as special light in addition to violet laser light and blue laser light, as shown in FIG. 29. The image of the object to be observed illuminated with the special light is picked up by the image pickup sensor 44, so that a special image consisting of Bs image signals, Gs image signals, and Rs image signals can be obtained. Pseudo white light may be light in which violet light V, blue light B, green light G, and red light emitted from the V-LED 20a, the B-LED 20b, the G-LED 20c, and the R-LED 20d are combined.

A phosphor including a plurality of types of phosphor that absorbs a part of blue laser light to excite and emit green light to yellow light (for example, YKG-based phosphors or phosphors, such as $BaMgAl_{10}O_{17}$ (BAM)) is preferably used as the phosphor 210. In a case where the semiconductor light emitting elements are used as the excitation light source of the phosphor 210 as in the present configuration example, high-intensity white light is obtained with high luminous efficacy. Accordingly, not only the intensity of white light can be easily adjusted but also a change in the color temperature and chromaticity of white light can be restrained to be small.

In the embodiments, although the present invention is applied to the endoscope system that performs processing on the endoscopic image which is one of the medical images, the present invention can also be applied to a medical image processing system that performs processing on medical images other than the endoscopic image. Further, the present invention can also be applied to a diagnosis support device that is used to provide diagnostic support to the user by using medical images. The present invention can also be applied to a medical service support device that is used to support the medical service, such as a diagnostic report, by using medical images.

Figure 30:
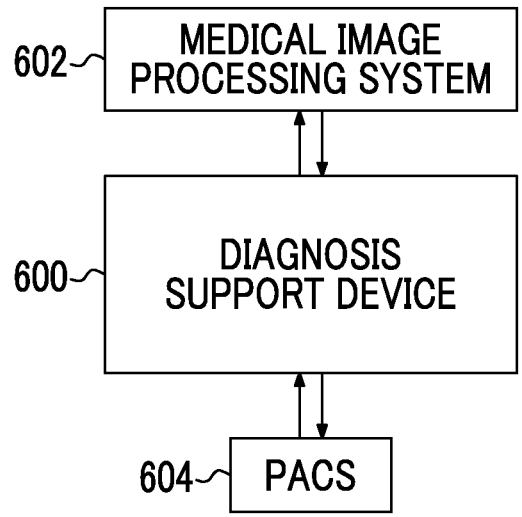
FIG. 30 is a block diagram showing a diagnosis support device.
Figure 31:
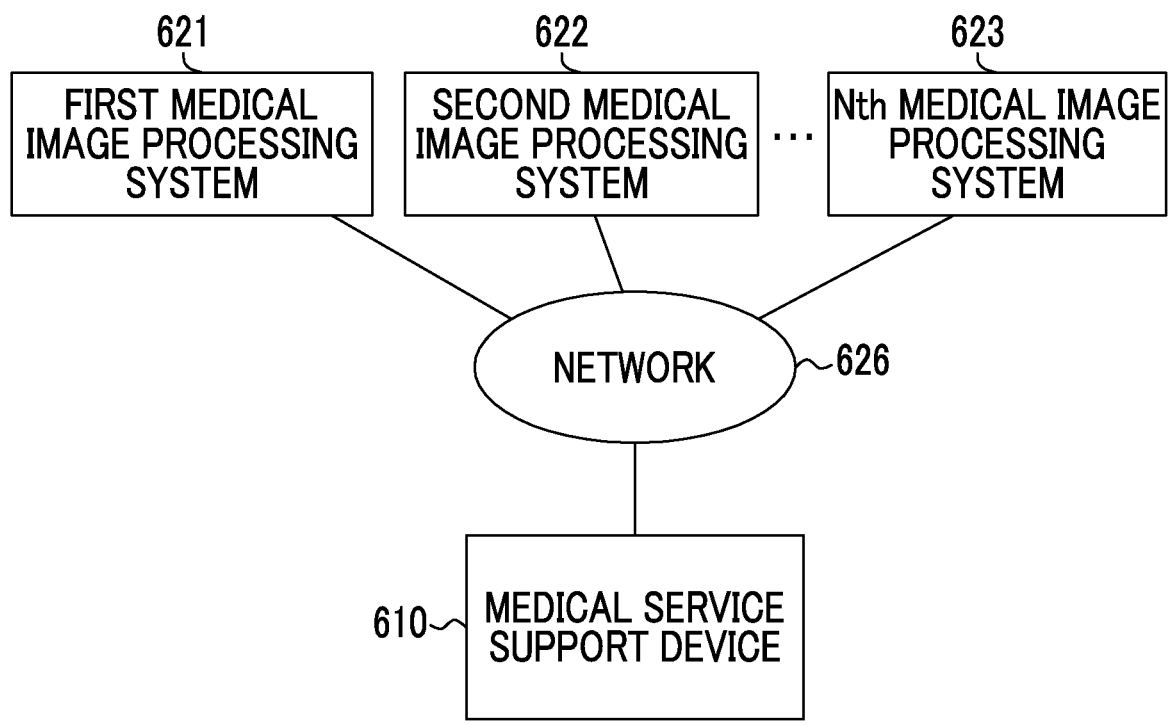
FIG. 31 is a block diagram showing a medical service support device.

For example, as shown in FIG. 30, a diagnosis support device 600 is used in combination with the modality, such as a medical image processing system 602, and picture archiving and communication systems (PACS) 604. As shown in FIG. 31, a medical service support device 610 is connected to various examination apparatuses such as a first medical image processing system 621, a second medical image processing system 622, . . . , and an Nth medical image processing system 623 through a certain network 626. The medical service support device 610 receives medical images from the first medical image processing system 621, the second medical image processing system 622, . . . , the Nth medical image processing system 623, and supports the medical service on the basis of the received medical images.

In the above-described embodiments, the hardware structures of processing units that execute various types of processing, such as the normal image generation unit 62, the special image generation unit 64, the disease-related processing unit 66, the spatial frequency component distribution calculation unit 71, the frequency characteristic region extraction unit 72, the first frequency characteristic region extraction unit 72a, the third frequency characteristic region extraction unit 72*b*, the analysis target region detection unit 72*c*, the second frequency characteristic region extraction unit 72*d*, the structure detection unit 74, the determination unit 76, the image processing implementation control unit 81, the magnification ratio index analysis unit 82, the halation distribution analysis unit 83, the frequency characteristic analysis unit 84, the brightness value analysis unit 85, the shadow distribution analysis unit 86, and the auxiliary measurement light analysis unit 87 that are included in the image processing unit 58, are various processors to be described below. The various processors include, for example, a central processing unit (CPU), which is a general-purpose processor that executes software (programs) to function as various processing units, a programmable logic device (PLD), such as a field programmable gate array (FPGA), which is a processor having a changeable circuit configuration after manufacture, and a dedicated electrical circuit, which is a processor having a dedicated circuit configuration designed to execute various processing.

One processing unit may be formed of one of these various processors, or may be formed of a combination of two or more processors (for example, a plurality of FPGAs, or a combination of a CPU and an FPGA) of the same type or different types. Alternatively, a plurality of processing units may be formed of one processor. A first example of the configuration in which a plurality of processing units are formed of one processor is an aspect in which one processor is formed of a combination of one or more CPUs and software and the processor functions as a plurality of processing units. A representative example of the aspect is a computer such as a client or a server. A second example of the configuration is an aspect in which a processor that implements all of the functions of a system including the plurality of processing units with one integrated circuit (IC) chip is used. A representative example of the aspect is a system on chip (SoC). In this manner, various processing units are formed of one or more of the above-described various processors as hardware structures.

More specifically, the hardware structures of these various processors are electrical circuitry in which circuit elements such as semiconductor elements are combined.

The present invention can also be implemented by the following alternative embodiment.

A processor device,
in which an image acquisition unit acquires a medical image obtained by picking up an image of an object to be observed;
an image processing decision unit decides whether or not to perform image processing on the medical image on the basis of an imaging condition of the medical image and/or an image analysis result obtained by analyzing the medical image; and
a disease-related processing unit performs, for the medical image on which the image processing decision unit has decided to perform the image processing, at least one of calculation of an index value related to a stage of ulcerative colitis, determination of the stage of the ulcerative colitis, or determination of the remission or non-remission of the ulcerative colitis, on the basis of denseness of superficial blood vessels, intramucosal hemorrhage, and extramucosal hemorrhage that are obtained from the medical image.

EXPLANATION OF REFERENCES

10: endoscope system
12: endoscope
12*a*: insertion part
12*b*: operation part
12*c*: bendable portion
12*d*: distal end portion
12*e*: angle knob
12*f*: mode changeover switch
12*g*: zoom operation portion
14: light source device
16: processor device
18: monitor
19: console
20: light source unit
20*a*: V-LED
20*b*: B-LED
20*c*: G-LED
20*d*: R-LED
21: light source control unit
23: optical path combination unit
25: light guide
30*a*: illumination optical system
30*b*: image pickup optical system
30*c*: lens for auxiliary measurement light
30*d*: auxiliary measurement light emitting unit
32: illumination lens
42: objective lens
44: image pickup sensor
45: image pickup control unit
46: CDS/AGC circuit
48: A/D converter
50: image acquisition unit
52: DSP
54: noise reduction unit
56: image processing switching unit
57: zoom control unit
58: image processing unit
60: video signal generation unit
62: normal image generation unit
64: special image generation unit
66: disease-related processing unit
70: image processing decision unit
71: spatial frequency component distribution calculation unit
72: frequency characteristic region extraction unit
72*a*: first frequency characteristic region extraction unit
72*b*: third frequency characteristic region extraction unit
72*c*: analysis target region detection unit
72*d*: second frequency characteristic region extraction unit
74: structure detection unit
76: determination unit
81: image processing implementation control unit
82: magnification ratio index analysis unit
83: halation distribution analysis unit
84: frequency characteristic analysis unit
85: brightness value analysis unit
86: shadow distribution analysis unit
87: auxiliary measurement light analysis unit
91, 95: monitor image
91*a*, 95*a*, 99, 100, 100*a*, 100*b*: special image
91*b*, 95*b*: halation distribution image
91*c*, 95*c*: spatial frequency distribution image
92: hood
92*a*: hood shadow region
93: magnification ratio display
96: halation region
97: high brightness region
98: low frequency region 101: endoscope system
102: broadband light source
104: rotary filter
105: filter switching unit
106: image pickup sensor
107: filter for normal light mode
107a: B filter
107b: G filter
107c: R filter
108: filter for special light mode and disease-related processing mode
108a: Bn filter
108b: Gn filter
200: endoscope system
203: violet laser light source unit
204: blue laser light source unit
208: light source control unit
210: phosphor
600: diagnosis support device
602: medical image processing system
604: PACS
610: medical service support device
621: first medical image processing system
622: second medical image processing system
623: Nth medical image processing system
626: network
SP, SP1, SP2: spot
Lm: optical axis
Rx: range
Px: near end
Py: near middle
Pz: far end
Qx, Qy, Qz: image pickup range
P1: position
Ax: optical axis
Dv: observation distance

What is claimed is:

1. An image processing device comprising:
a processor configured to:
   acquire a medical image obtained by picking up an image of an object to be observed,
   decide whether or not to perform image processing on the medical image on the basis of an imaging condition of the medical image and/or an image analysis result obtained by analyzing the medical image, and
   perform, for the medical image on which the processor has decided to perform the image processing, at least one of calculation of an index value related to a stage of ulcerative colitis, determination of the stage of the ulcerative colitis, or determination of remission or non-remission of the ulcerative colitis on the basis of denseness of superficial blood vessels, intramucosal hemorrhage, and extramucosal hemorrhage that are obtained from the medical image.

2. The image processing device according to claim 1, wherein the imaging condition of the medical image is a magnification ratio index of the medical image.

3. The image processing device according to claim 1, wherein the image analysis result is at least one of a halation distribution, a frequency characteristic, a brightness value, or a shadow distribution that is obtained from the medical image.

4. The image processing device according to claim 1, wherein the medical image is obtained by picking up the image of the object to be observed irradiated with auxiliary measurement light which is used to measure the object to be observed, and the image analysis result is a position of an auxiliary measurement light irradiation region formed on the object to be observed in the medical image.

5. The image processing device according to claim 1, wherein the processor is configured to perform, for the medical image on which the processor has decided to perform the image processing, at least one of the calculation of the index value related to the stage of the ulcerative colitis, the determination of the stage of the ulcerative colitis, or the determination of the remission or non-remission of the ulcerative colitis on the basis of the imaging condition of the medical image and/or the image analysis result obtained by analyzing the medical image.

6. The image processing device according to claim 1, wherein the processor is configured to, in a case where the processor determines the remission or non-remission of the ulcerative colitis, classify the denseness of the superficial blood vessels, the intramucosal hemorrhage, and the extramucosal hemorrhage depending on a frequency characteristic or a brightness value that is obtained from the medical image and determines the remission or non-remission of the ulcerative colitis according to the classification.

7. The image processing device according to claim 1, wherein the processor is configured to perform, in a case where the processor determines the remission or non-remission of the ulcerative colitis:
   calculate a spatial frequency component distribution from the medical image;
   extract a first frequency characteristic region having a first frequency characteristic, extracts a second frequency characteristic region having a second frequency characteristic of which a frequency is higher than a frequency of the first frequency characteristic, and extracts a third frequency characteristic region having a third frequency characteristic of which a frequency is higher than the frequency of the second frequency characteristic, on the basis of the spatial frequency component distribution;
   detect the denseness of the superficial blood vessels, the intramucosal hemorrhage, and the extramucosal hemorrhage on the basis of the first frequency characteristic region that is subjected to first region discrimination processing using a brightness value, the second frequency characteristic region that is subjected to second region discrimination processing using a brightness value, and the third frequency characteristic region; and
   determine the remission or non-remission of the ulcerative colitis on the basis of the denseness of the superficial blood vessels, the intramucosal hemorrhage, and the extramucosal hemorrhage.

8. The image processing device according to claim 1, wherein the medical image is obtained by picking up the image of the object to be observed illuminated with illumination light including short-wavelength light.

9. The image processing device according to claim 8, wherein the illumination light is violet light of which a central wavelength or a peak wavelength includes a wavelength of 410 nm.

10. A method of operating an image processing device including a processor, the method comprising:
   an image acquisition step of, by the processor, acquiring a medical image obtained by picking up an image of an object to be observed;

an image processing decision step of, by the processor, deciding whether or not to perform image processing on the medical image on the basis of an imaging condition of the medical image or an image analysis result obtained by analyzing the medical image; and a determination step of, by the processor, performing, for the medical image on which the processor has decided to perform the image processing, at least one of calculation of an index value related to a stage of ulcerative colitis, determination of the stage of the ulcerative colitis, or determination of remission or non-remission of the ulcerative colitis on the basis of denseness of superficial blood vessels, intramucosal hemorrhage, and extramucosal hemorrhage that are obtained from the medical image.

11. The method of operating an image processing device according to claim 10, wherein the determination step includes, in a case where the remission or non-remission of the ulcerative colitis is determined by the processor in the determination step:

a step of, by the processor, calculating a spatial frequency component distribution from the medical image;

a step of, by the processor, extracting a first frequency characteristic region having a first frequency characteristic, extracting a second frequency characteristic region having a second frequency characteristic of which a frequency is higher than a frequency of the first frequency characteristic, and extracting a third frequency characteristic region having a third frequency characteristic of which a frequency is higher than the frequency of the second frequency characteristic, on the basis of the spatial frequency component distribution;

a step of, by the processor, detecting the denseness of the superficial blood vessels, the intramucosal hemorrhage, and the extramucosal hemorrhage on the basis of the first frequency characteristic region that is subjected to first region discrimination processing using a brightness value, the second frequency characteristic region that is subjected to second region discrimination processing using a brightness value, and the third frequency characteristic region; and a step of, by the processor, determining the remission or non-remission of the ulcerative colitis on the basis of the denseness of the superficial blood vessels, the intramucosal hemorrhage, and the extramucosal hemorrhage.

12. The method of operating an image processing device according to claim 10, wherein the medical image is obtained by picking up the image of the object to be observed illuminated with illumination light that is violet light of which a central wavelength or a peak wavelength includes a wavelength of 410 nm.

* * * * *